US012605535B2

(12) United States Patent
Sinha et al.

(10) Patent No.: US 12,605,535 B2
(45) Date of Patent: Apr. 21, 2026

(54) DURABLE IMPLANTABLE NON-OBSTRUCTIVE VENOUS ASSIST DEVICE FOR SUPPORT OF CAVOPULMONARY FONTAN CIRCULATION

(71) Applicant: CHILDREN'S NATIONAL MEDICAL CENTER, Washington, DC (US)

(72) Inventors: Pranava Sinha, Arlington, VA (US); William A. Smith, Lyndhurst, OH (US); Stephan Weber, Lyndhurst, OH (US)

(73) Assignee: Children's National Medical Center, Washington, DC (US)

( * ) Notice: Subject to any disclaimer, the term of this patent is extended or adjusted under 35 U.S.C. 154(b) by 967 days.

(21) Appl. No.: 17/790,023

(22) PCT Filed: Dec. 28, 2020

(86) PCT No.: PCT/US2020/067109
§ 371 (c)(1),
(2) Date: Jun. 29, 2022

(87) PCT Pub. No.: WO2021/138233
PCT Pub. Date: Jul. 8, 2021

(65) Prior Publication Data
US 2023/0037926 A1 Feb. 9, 2023

Related U.S. Application Data

(60) Provisional application No. 62/955,593, filed on Dec. 31, 2019.

(51) Int. Cl.
*A61M 60/148* (2021.01)
*A61M 60/237* (2021.01)
(Continued)

(52) U.S. Cl.
CPC ........ *A61M 60/148* (2021.01); *A61M 60/237* (2021.01); *A61M 60/35* (2021.01);
(Continued)

(58) Field of Classification Search
CPC .. A61M 60/148; A61M 60/237; A61M 60/35; A61M 60/422; A61M 60/806;
(Continued)

(56) References Cited

U.S. PATENT DOCUMENTS 7,811,244 B2 10/2010 Dasi et al.
8,177,703 B2 5/2012 Smith et al.
(Continued)

FOREIGN PATENT DOCUMENTS

EP 3398626 11/2018
WO 2005020848 A2 3/2005
WO 20170217946 12/2017

OTHER PUBLICATIONS

International Search Report and Written Opinion in PCT/US2020/067109. Mailed Mar. 8, 2021. 10 pages.
(Continued)

*Primary Examiner* — Thomas C Barrett
*Assistant Examiner* — Jose H. Trevino, III
(74) *Attorney, Agent, or Firm* — Meunier Carlin & Curfman LLC

(57) ABSTRACT

The circulation assist devices disclosed herein can be used, for example, in methods of decreasing venous pressure in the Fontan circulation. The devices can include an inlet, an outlet, a stator, a rotor, and an impeller driven by rotation of the rotor. In some embodiments, the impeller blade (or blades) can at least partially define a central lumen extending through the device. The device can be coupled to the inferior vena cava and the pulmonary artery. Rotating the impeller blade(s) increases blood velocity through the lumen
(Continued)

and causes the outlet pressure to be higher than the inlet pressure. The impeller can be configured such that, when it is stationary, the forward static pressure drop between the inlet and the outlet is minimized. That is, the forward static pressure drop of the device approximates the pressure drop between the inferior vena cava and central pulmonary artery of the unassisted Fontan circulation.

19 Claims, 19 Drawing Sheets

(51) Int. Cl.
| | |
|---|---|
| *A61M 60/35* | (2021.01) |
| *A61M 60/422* | (2021.01) |
| *A61M 60/806* | (2021.01) |
| *A61M 60/824* | (2021.01) |
| *A61M 60/827* | (2021.01) |

(52) U.S. Cl.
CPC ........ *A61M 60/422* (2021.01); *A61M 60/806* (2021.01); *A61M 60/824* (2021.01); *A61M 60/827* (2021.01)

(58) Field of Classification Search
CPC .............. A61M 60/824; A61M 60/827; A61M 60/804; A61M 60/812; A61M 60/462; A61M 60/459; A61M 60/457; A61M 60/416; A61M 60/82; A61M 60/216; A61M 2205/04; A61M 2210/125; A61M 60/411; A61M 60/122; A61M 60/165; A61M 60/419; A61M 60/495; A61M 60/441; A61M 60/104; A61M 60/289; A61M 60/205; A61M 60/232; A61M 60/196

See application file for complete search history.

(56) References Cited

U.S. PATENT DOCUMENTS

| | | | | |
|---|---|---|---|---|
| 8,777,832 | B1 | 7/2014 | Wang et al. | |
| 8,992,407 | B2 | 3/2015 | Smith et al. | |
| 9,227,002 | B1 | 1/2016 | Giridharan et al. | |
| 2001/0009645 | A1 | 7/2001 | Noda | |
| 2005/0147512 | A1 | 7/2005 | Chen et al. | |
| 2011/0257462 | A1 | 10/2011 | Rodefeld et al. | |
| 2013/0209292 | A1* | 8/2013 | Baykut ............... | A61M 60/806 |
| | | | | 415/73 |
| 2014/0275724 | A1 | 9/2014 | Wang et al. | |
| 2016/0271309 | A1 | 9/2016 | Throckmorton et al. | |
| 2018/0058437 | A1 | 3/2018 | Eilers et al. | |
| 2018/0256794 | A1* | 9/2018 | Rodefeld .............. | A61M 60/35 |

OTHER PUBLICATIONS

Anderson PAW, Sleeper LA, Mahony L, Colan SD, Atz AM, Breitbart RE, Gersony WM, Gallagher D, Geva T, Margossian R et al: Contemporary Outcomes After the Fontan ProcedureA Pediatric Heart Network Multicenter Study. Journal of the American College of Cardiology 2008, 52(2):85-98.

ASTM F1841-97(2013), Standard Practice for Assessment of Hemolysis in Continuous Flow Blood Pumps, ASTM International, West Conshohocken, PA, 2013.

Chopski SG, Fox CS, McKenna KL, Riddle ML, Kafagy DH, Stevens RM, Throckmorton AL. Physics-driven impeller designs for a novel intravascular blood pump for patients with congenital heart disease. Med Eng Phys. Jul. 2016;38(7):622-32.

Chopski SG, Rangus OM, Moskowitz WB, Throckmorton AL. Experimental measurements of energy augmentation for mechanical circulatory assistance in a patient-specific Fontan model. Artif Organs. Sep. 2014;38(9):791-9.

D'Udekem Y, Iyengar AJ, Cochrane AD, Grigg LE, Ramsay JM, Wheaton GR, Penny DJ, Brizard CP: The Fontan Procedure: Contemporary Techniques Have Improved Long-Term Outcomes. Circulation 2007, 116(11 suppl):I-157-I-164.

Diller G-P, Giardini A, Dimopoulos K, Gargiulo G, Müller J, Derrick G, Giannakoulas G, Khambadkone S, Lammers AE, Picchio FM et al: Predictors of morbidity and mortality in contemporary Fontan patients: results from a multicenter study including cardiopulmonary exercise testing in 321 patients. European Heart Journal 2010, 31(24):3073-3083.

Fukamachi K, Saeed D, Massiello AL, Horvath DJ, Fumoto H, Horai T, Zahr R, Shalli S, Anzai T, Dessoffy R, Catanese J, Chen J-F, Zhou Q, Benefit S, Alfini S, Golding Larg. Development of DexAide Right Ventricular Assist Device: Update II ASAIO J. 2008; 54(6): 589-593.

Giridharan GA, Ising M, Sobieski MA, Koenig SC, Chen J, Frankel S, Rodefeld MD. Cavopulmonary assist for the failing Fontan circulation: impact of ventricular function on mechanical support strategy. ASAIO J. Nov.-Dec. 2014;60(6):707-15.

Giridharan GA, Koenig SC, Kennington J, Sobieski MA, Chen J, Frankel SH, Rodefeld MD. Performance evaluation of a pediatric viscous impeller pump for Fontan cavopulmonary assist. J Thorac Cardiovasc Surg. Jan. 2013;145(1):249-57. 22421403.

Gu L, Smith WA. Evaluation of computational models for hemolysis estimation. ASAIO J. May-Jun. 2005;51(3):202-7.

Herbertson LH, Olia SE, Daly A, Noatch CP, Smith WA, Kameneva MV, Malinauskas RA. Multilaboratory study of flow-induced hemolysis using the FDA benchmark nozzle model. Artif Organs. Mar. 2015;39(3):237-48.

Kafagy DH, Dwyer TW, McKenna KL, Mulles JP, Chopski SG, Moskowitz WB, Throckmorton AL. Design of axial blood pumps for patients with dysfunctional fontan physiology: computational studies and performance testing. Artif Organs. Jan. 2015;39(1):34-42.

Kawahito K, Nose Y. Hemolysis in different centrifugal pumps. Artif Organs 1997;21:323-326.

Khairy P, Fernandes SM, Mayer JE, Jr., Triedman JK, Walsh EP, Lock JE, Landzberg MJ: Long-term survival, modes of death, and predictors of mortality in patients with Fontan surgery. Circulation 2008, 117(1):85-92.

Kirklin JK, Naftel DC, Pagani FD, Kormos RL, Stevenson L, Miller M, Young JB: Long-term mechanical circulatory support (destination therapy): on track to compete with heart transplantation? The Journal of thoracic and cardiovascular surgery 2012, 144(3):584-603; discussion 597-588.

Koller T Jr, Hawrylenko A. Contribution to the in vitro testing of pumps for extracorporeal circulation. J Thorac Cardiovasc Surg. Jul. 1967;54(1):22-9.

Lacour-Gayet FG, Lanning CJ, Stoica S, Wang R, Rech BA, Goldberg S, Shandas R. An artificial right ventricle for failing fontan: in vitro and computational study. Ann Thorac Surg. Jul. 2009;88(1):170-6.

Malanoski SB, Belawski H, Horvath D, Smith WA, Golding LR. Stable blood lubricated hydrodynamic journal bearing with magnetic loading. ASAIO J 1998;44:M737-740.

Malinauskas RA. Plasma hemoglobin measurement techniques for the in vitro evaluation of blood damage caused by medical devices. Artif Organs. Dec. 1997;21(12):1255-67.

McCrindle BW, Manlhiot C, Cochrane A, et al. Factors associated with thrombotic complications after the Fontan procedure: a secondary analysis of a multicenter, randomized trial of primary thromboprophylaxis for 2 years after the Fontan procedure. Journal of the American College of Cardiology Jan. 22, 2013;61(3):346-53.

Naito K, Mizuguchi K, Nosé Y. The need for standardizing the index of hemolysis. Artif Organs. Jan. 1994;18(1):7-10.

Naito K, Suenaga E, Cao ZL, Suda H, Ueno T, Natsuaki M, Itoh T. Comparative hemolysis study of clinically available centrifugal pumps. Artif Organs 1996;20:560-563.

Paridon SM, Mitchell PD, Colan SD, Williams RV, Blaufox A, Li JS, Margossian R, Mital S, Russell J, Rhodes J: A Cross-Sectional Study of Exercise Performance During the First 2 Decades of Life After the Fontan Operation. Journal of the American College of Cardiology 2008, 52(2):99-107.

(56)                References Cited

OTHER PUBLICATIONS

Park SJ, Milano CA, Tatooles AJ, Rogers JG, Adamson RM, Steidley DE, Ewald GA, Sundareswaran KS, Farrar DJ, Slaughter MS et al: Outcomes in Advanced Heart Failure Patients With Left Ventricular Assist Devices for Destination Therapy / Clinical Perspective. Circulation: Heart Failure 2012, 5(2):241-248.

Potapov E, Schweiger M, Vierecke J, Dandel M, Stepanenko A, Kukucka M, Jurmann B, Hetzer R, Krabatsch T. Discontinuation of HeartWare RVAD support without device removal in chronic BIVAD patients. ASAIO J 2012;58:15-18.

Rodefeld MD, Boyd JH, Myers CD, LaLone BJ, Bezruczko AJ, Potter AW, Brown JW. Cavopulmonary assist: circulatory support for the univentricular Fontan circulation. Ann Thorac Surg. Dec. 2003;76(6):1911-6; discussion 1916.

Rodefeld MD, Coats B, Fisher T, Giridharan GA, Chen J, Brown JW, Frankel SH: Cavopulmonary assist for the univentricular Fontan circulation: von Karman viscous impeller pump. The Journal of thoracic and cardiovascular surgery 2010, 140(3):529-536.

Rose EA, Gelijns AC, Moskowitz AJ, Heitjan DF, Stevenson LW, Dembitsky W, Long JW, Ascheim DD, Tierney AR, Levitan RG et al: Long-Term Use of a Left Ventricular Assist Device for End-Stage Heart Failure. New England Journal of Medicine 2001, 345(20):1435-1443.

Sinha P, Deutsch N, Ratnayaka K, Lederman R, He D, Nuszkowski M, Montague E, Mikesell G, Ishibashi N, Zurakowski D, Jonas R. Effect of mechanical assistance of the systemic ventricle in single ventricle circulation with cavopulmonary connection. The Journal of thoracic and cardiovascular surgery. 2014;147:1271-1275.

Sinha P, Zurakowski D, He D, Yerebakan C, Freedenberg V, Moak JP, Jonas RA: Intra/extracardiac fenestrated modification leads to lower incidence of arrhythmias after the Fontan operation. The Journal of thoracic and cardiovascular surgery 2013, 145(3):678-682.

Slaughter MS, Rogers JG, Milano CA, Russell SD, Conte JV, Feldman D, Sun B, Tatooles AJ, Delgado RM, Long JW et al: Advanced Heart Failure Treated with Continuous-Flow Left Ventricular Assist Device. New England Journal of Medicine 2009, 361(23):2241-2251.

Steines D, Westphal D, Gobel C, Reul H, Rau G. Platelet function and hemolysis in centrifugal pumps: in vitro investigations. Int J Artif Organs 1999;22:559-565.

Stephenson EA, Lu M, Berul CI, Etheridge SP, Idriss SF, Margossian R, Reed JH, Prakash A, Sleeper LA, Vetter VL et al: Arrhythmias in a contemporary fontan cohort: prevalence and clinical associations in a multicenter cross-sectional study. Journal of the American College of Cardiology 2010, 56(11):890-896.

International Preliminary Report on Patentability issued for Application No. PCTUS2020067109, dated Jul. 14, 2022.

* cited by examiner

53

57

55

55

53

57

59

55

NOVAD Pump Model Comparison of Solid Impeller with Cored Impeller Input Power vs. Flow

DURABLE IMPLANTABLE NON-OBSTRUCTIVE VENOUS ASSIST DEVICE FOR SUPPORT OF CAVOPULMONARY FONTAN CIRCULATION

RELATED APPLICATIONS

This application is a national stage application filed under 35 U.S.C. § 371 of PCT/US2020/067109, filed on Dec. 28, 2020, which claims the benefit of U.S. Provisional Application 62/955,593, filed Dec. 31, 2019. Each of the aforementioned applications is incorporated by reference in its entirety for all purposes.

STATEMENT REGARDING FEDERALLY SPONSORED RESEARCH OR DEVELOPMENT

This invention was made with Government Support under Grant No. 1R43HL137453-01 awarded by the National Institutes of Health. The Government has certain rights in the invention.

FIELD

This invention relates to circulation assist devices, and more particularly to those for supporting single ventricle patients.

BACKGROUND

The single ventricle palliation pathway addresses all congenital heart defects that are not amenable to establishment of a normal two-ventricle circulation. This involves a series of surgical diversions to allow all blood returning from the body to directly and passively flow into the low resistance circuit of the lungs, while the solitary ventricle is used to pump blood into the higher resistance body (systemic) circuit. This is done in a stepwise fashion with diversion of the blood flow from the upper body via the superior vena cava (SVC) to the lungs initially (Bidirectional Glenn circulation) followed by addition of the blood from the lower body via the inferior vena cava (IVC) to the lungs (Fontan circulation). FIG. 16 shows a diagram of a conventional Fontan circulation after the surgical procedure is complete. The Fontan operation comprises about 8.5% of the approximately 10,000 congenital cardiac surgical procedures performed in the US annually [1]. Significant improvements in the outcomes of the Fontan operation [2] and improved long term survival in these patients [3-7] have led to a large number of these patients now surviving to early adulthood. While this is a viable circulation, absence of a ventricle to pump blood to the lungs limits the efficiency of this circulation, and inherent inefficiencies of the Fontan circulation result in suboptimal exercise capacity [4, 6], long-term morbidity [3, 4, 6, 7] and late mortality [4, 5]. Delayed failure of the Fontan circulation is seen almost 30% of these patients at 15 years [8]. In addition to overall low cardiac output, these patients also have chronically elevated venous pressure leading to congestive changes in their liver and gut, which presents as hepatic fibrosis/cirrhosis and protein losing enteropathy. Presently the only viable management option for these patients is heart transplantation, which is already limited by donor constraints.

SUMMARY

The circulation assist device disclosed herein addresses the problems presented by single ventricle palliation pathways, and specifically, the Fontan circulation pathway. It can be utilized as a direct replacement for the inferior vena cava of the Fontan circulation, for example, in place of the interposition grafts currently used to connect the inferior vena cava to the pulmonary artery at the cavopulmonary junction. In this way, it alleviates systemic venous pressure while providing additional support to the single ventricle. The circulation assist device includes an inlet, an outlet, a central longitudinal axis extending between the inlet and the outlet, a stator having at least one stator coil, a rotor having at least one rotor magnet, and an impeller driven by rotation of the rotor.

The impeller has at least one impeller blade and at least partially defines a lumen of the circulation assist device. Activation of the at least one stator coil causes rotation of the rotor relative to the stator, thereby driving rotation of the impeller. When the impeller is stationary, the forward static pressure drops between the inlet and the outlet of the circulation assist device is minimized (such that the forward static pressure drop approximates the pressure drop between the inferior vena cava and central pulmonary artery of the unassisted Fontan circulation). This minimizes risk to the patient should the central assist device fail during use. In some embodiments, the lumen partially defined by the impeller extends between the inlet and the outlet of the circulation assist device along the central longitudinal axis. The impeller can be positioned radially inward from the rotor. The impeller can have a radially external side and a radially internal side, with a portion of the radially internal side of the impeller being radially spaced from a central longitudinal axis and at least partially defining the central lumen. In some embodiments, the circulation assist device includes an axially extending void as part of the central lumen, with the impeller blade extending helically around the axially extending void. In some embodiments, the forward static pressure drop is no greater than 5 mmHg for flows up to 3 L/min when the impeller is stationary. In some embodiments, the circulation assist device is configured to give a forward pressure rise of greater than 10 mmHg when the impeller is rotating. The circulation assist device can be sized to fit within the vasculature of an animal subject.

In some embodiments, the rotor includes a drive magnet that magnetically couples to a driven magnet on at least one impeller blade. The driven magnet can be radially offset from the drive magnet. The magnetic coupling enables the rotation of the rotor to drive the rotation of the impeller. In some embodiments, the magnetic coupling between the drive and driven magnets offsets a hydraulic thrust on the impeller. In some embodiments, the functions of the rotor and the impeller are integrated into a single component.

The impeller blade can be shaped to smoothly accelerate blood traveling between the inlet and the outlet. In some embodiments, the leading edge of the impeller blade can have a varying attack angle relative to the central longitudinal axis, such that the blade velocity at any radius approximates the laminar velocity of entering blood at that radius. An attack angle formed between an upstream surface of the impeller blade and the central longitudinal axis can vary radially. In some embodiments, the helix angle of the impeller blade varies longitudinally.

In some embodiments, the thickness of the impeller blade is greater at a radially external side than a radially internal side.

In some embodiments, the impeller can be supported radially by a hydrodynamic bearing.

In some embodiments, the impeller can include an axle coupled to the at least one impeller blade. The length of the axle can be shorter than the length of the impeller (reducing physical structure within the central lumen). In some embodiments, the impeller further comprises a second axle longitudinally spaced downstream from the first axle. The impeller blade can be coupled to the first axle, can bridge an axially extending void between the first and second axle, and can couple to the second axle. The axle(s) can be configured to provide axial thrust stop(s) in cooperation with a stationary stop on the impeller housing.

In some embodiments, the circulation assist device can include an axle support that stabilizes the impeller axle along the central longitudinal axis. The axle support can extend radially inward between an inner surface of a stationary impeller housing and the central longitudinal axis. In some embodiments, the axle support extends at least partially around the impeller axle in a circumferential direction.

Some embodiments can also include a sealing wall positioned between the rotor and the impeller. The sealing wall serves to isolate the rotor and the stator from blood traveling through the central lumen.

Some embodiments can include an impeller housing that is stationary with respect to the stator during rotation of the rotor and impeller. The impeller housing can include at least one stationary inlet guide vane and at least one stationary outlet guide vane.

Some embodiments can include a power source configured to provide electricity to the stator coil. The power source can include a battery.

In some embodiments, at least one blood contacting surface is coated with a low drag, high blood compatibility coating. The coating can be, for example, polytetrafluoroethylene (PTFE). In some embodiments, all blood contacting surfaces are coated with the coating.

Methods are disclosed herein for decreasing venous pressure in the Fontan circulation. The methods include establishing a first fluidic coupling between the inferior vena cava and an inlet of a circulation assist device, establishing a second fluidic coupling between the central pulmonary artery and an outlet of the circulation assist device, moving blood through the inlet of the circulation assist device at an inlet velocity and an inlet pressure, moving blood through a central lumen of the circulation assist device, rotating at least one rotatable impeller blade to increase blood velocity through the central lumen, and moving blood through the outlet at an outlet velocity and an outlet pressure.

The outlet pressure is higher than the inlet pressure when the impeller is rotating. In some embodiments, the outlet pressure is higher than the inlet pressure by greater than 10 mmHg for pump induced forward flow equal or greater than 3 L/min. When the impeller is not rotating, the forward static pressure drop between the inlet and the outlet of the circulation assist device approximates the pressure drop between the inferior vena cava and central pulmonary artery of the unassisted Fontan circulation. In some embodiments, the forward static pressure drop is no greater than 5 mmHg for flows up to 3 L/min when the impeller is stationary.

In some embodiments of the methods, moving blood through a central lumen can include moving blood through an axially extending void entirely devoid of structure. In some embodiments of the methods, moving blood through a central lumen can include moving blood past at least one stationary inlet guide vane and at least one stationary outlet guide vane.

In some embodiments of the methods, the first fluidic coupling is made established between the caudal intrapericardial inferior vena cava and an inlet of a circulation assist device. The circulation assist device can be configured to serve as a direct replacement for the inferior vena cava in the Fontan circulation. In some embodiments of the methods, a second circulation assist device can be utilized as a direct replacement for the superior vena cava in the Fontan circulation.

DESCRIPTION OF DRAWINGS

The device is explained in even greater detail in the following drawings. The drawings are merely exemplary to illustrate the structure of garments and certain features that may be used singularly or in combination with other features. The drawings are not necessarily drawn to scale.

DETAILED DESCRIPTION

Figure 1:
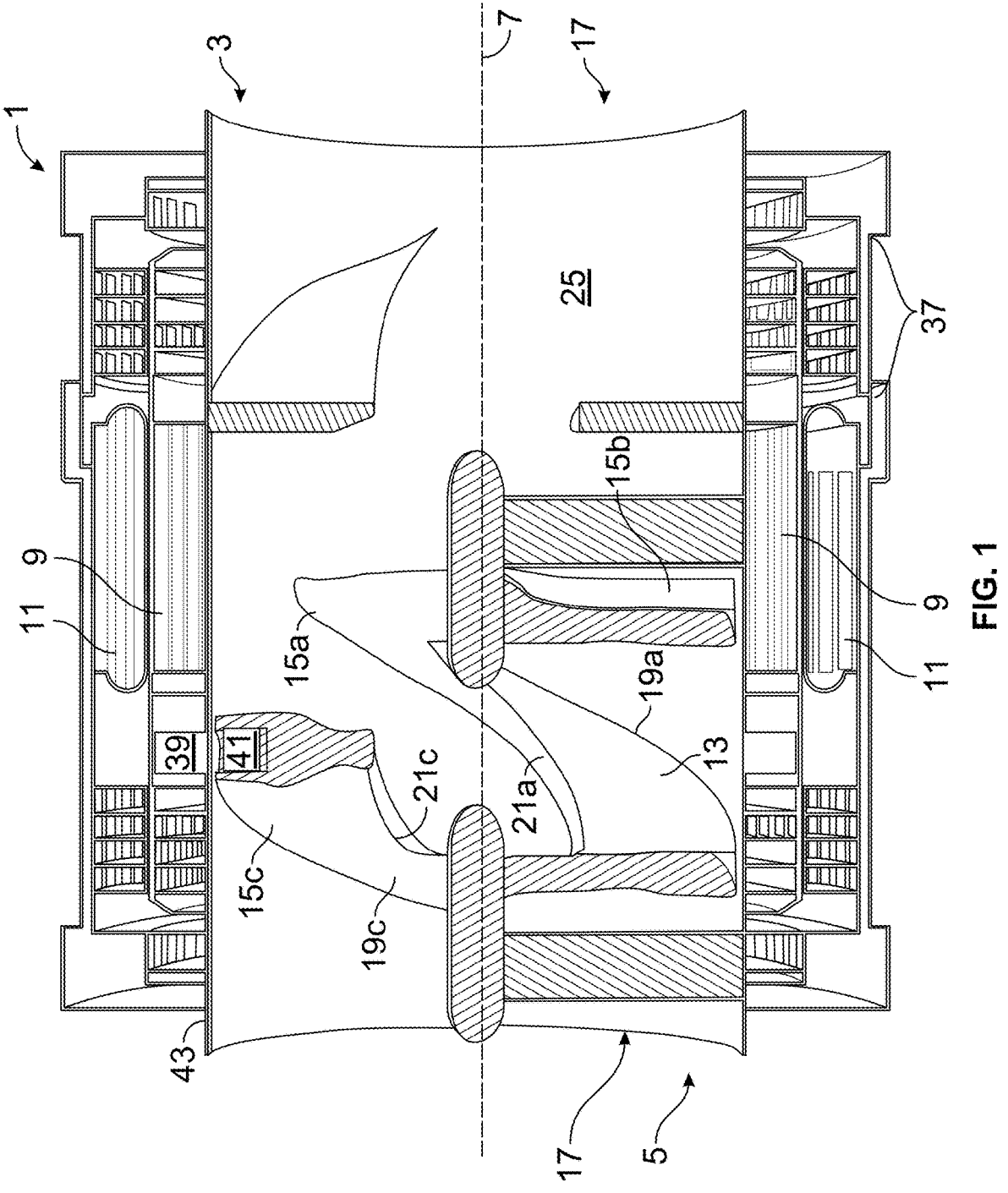
FIG. 1 shows a cross-sectional view of an embodiment of the circulation assist device.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

Throughout this application, various publications and patent applications are referenced. The disclosures of these publications in their entireties are hereby incorporated by reference into this application in order to more fully describe the state of the art to which this disclosure pertains. However, it should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. The terms "about" and "approximately" are defined as being "close to" as understood by one of ordinary skill in the art. In one non-limiting embodiment the terms are defined to be within 10%. In another non-limiting embodiment, the terms are defined to be within 5%. In still another non-limiting embodiment, the terms are defined to be within 1%.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

As used herein, components of the circulation assist device positioned upstream are contacted by a fluid (blood, for example) before items positioned downstream. Upstream components are closer to the inlet of the circulation assist device than downstream components, and downstream components are closer to the outlet of the circulation assist device than upstream components. Furthermore, "leading" and "trailing" refer to regions of the impeller, spaced from each other along the longitudinal axis, with "leading" referring to the upstream region and "trailing" referring to the downstream region of the impeller. "Forward" indicates the direction fluid flows through the circulation assist device (upstream to downstream). The terms "pressure rise" and "pressure drop" compare the pressure at the outlet of the circulation assist device to the pressure at the inlet. A pressure rise, or a forward pressure rise, indicates that the pressure is higher at the outlet of the circulation assist device than at the inlet of the circulation assist device. A pressure drop, or a forward pressure drop, indicates the pressure is lower at the outlet of the circulation assist device than at the inlet of the circulation assist device. A static forward pressure drop indicates a pressure drop when the impeller is stationary. The terms "pump" and "circulation assist device" may be used interchangeably.

Placing a device within the venous circuit will invariably cause an increased pressure gradient. Generally, a pressure gradient of <2-3 mmHg is considered non-significant in the venous circuit. A pressure gradient of 3-4 mmHg may be suggestive of venous obstruction, depending on other factors. A pressure gradient>5 mmHg is considered an indication of venous obstruction. As such, the disclosed device is configured to induce a forward static pressure drop of no greater than 5 mmHg at 3 L/min flows, and preferably less than about 3 mmHg. In terms of percentage drop (relative to average Fontan pressure of about 15 mmHg) it is about 20% of baseline.

The forward static pressure drop of the circulation assist device disclosed herein approximates, or is only slightly greater than, the native pressure drop between the inferior vena cava and central pulmonary artery of the native Fontan circulation. As used herein, the term "approximates" means the first measurement (forward static pressure drop with circulation assist device in place at the cavopulmonary juncture) differs from the second measurement (native, unassisted pressure drop between the IVC and CPA in the Fontan circulation) by a value less than about 20 percent. In certain embodiments, the first measurement differs from the second measurement by less than 18 percent, less than 16 percent, less than 14 percent, less than 12 percent, less than 10 percent, less than 8 percent, less than 6 percent, less than 4 percent, or less than 2 percent.

As stated in the background, there exists a need for circulation assist devices designed specifically for single ventricle patients, and patients with Fontan circulation. Patients with heart failure but normal anatomy can be adequately managed with conventional ventricular assist devices providing mechanical circulatory support [9, 10] while they are awaiting heart transplantation (bridge to transplantation) or in some instances as the definitive therapy (destination therapy) [11, 12]. However, these pumps overpower the venous system in congenital heart defect patients, and generally require heavy anticoagulation. Furthermore, the anatomy of the single ventricle circulation presents special challenges in providing mechanical circulatory support effectively. Particularly, pumps designed to assist the normal anatomy typically bypass the native circulation. As such, pumps designed to bypass the failing normal circulation are designed without consideration of resistance to passive flow. It is not desirable to have any backflow through pumps designed to assist the normal anatomy, and there is no passive flow in these circuits. The normal-anatomy pumps are designed to run as efficient as possible, but resistance to passive flow is not a consideration as a failing or turned off pump usually means life threatening problems for the patient. On the contrary, a pump designed to assist the Fontan circulation, being placed in series with the circulation, needs to have low resistance to passive flow so that, in the event the pump fails, the native Fontan circulation takes over and the failed pump is not a major obstruction to venous flow in the short term, allowing for sufficient time to design and implement clinical response strategies. A distinguishing feature of the circulation assist device disclosed herein is the redundancy of the system, with the pump providing minimal resistance to blood flow in a passive state so that in case of system failure the patient will revert automatically to an unassisted Fontan circulation.

Mechanical circulatory support to a single ventricle Fontan circulation can be broadly grouped into one of the two strategies: PUSH [13] by providing a mechanical pump instead of the right ventricle or PULL [14] by providing additional support to the single ventricle. While the pull strategy effectively increases the cardiac output, it is ineffective in improving venous congestion. The push strategy on the other hand with even the currently innovative pumps [13] has the drawback of not being universally applicable to all patients depending on the amount of superior vena cava (SVC) and inferior vena cava (IVC) offset, and the risk of increasing circuit pressure drop with no redundancy in an event of pump failure. Any intraluminal body in the lumen of the low pressure, low velocity Fontan circuit prone to thrombosis [15], is likely to risk clotting of the entire pathway with serious detriment to the patient, even death.

One approach inserts a spinning, vaned, bi-conical rotor with no housing at the junction of the Fontan circulation [13, 16-18]. However, the rotor lies in the center of the circulation path and, should it fail, would present an obstruction to venous flow.

Some attempts to improve outcomes for Fontan patients make use of catheter pumps. However, a catheter pump requires purge flow for cable lubrication and cable exit/ blood interface sealing which has important issues with patient fluid loading, contamination of the purge fluid, and interruption of the purge leading to thrombosis, catheter mechanical damage and failure. Thrombosis at the vein puncture site or along the catheter track within the venous system is a risk. To prevent drive cable kinking, the catheter sheath has to be relatively stiff, at least compared to current clinical VADs, leading to skin exit infection concerns and post implant patient mobilization issues.

Another group has proposed a collapsible axial flow pump enclosed by a stent, an assembly of two pumps intended to be expanded against the IVC and SVC walls after positioning [19-21]. A test of a non-collapsible pump version suggests hydraulic performance will be appropriate. Static pressure drop is not addressed. This is again a catheter pump, with all of the associated issues described above.

Another reference describes an axial flow pump concept that was tested using computational fluid dynamics and in vitro mock circuits of Fontan circulation. The device met threshold and flows and a static pressure drop of 2 mmHg at 4 L of passive flow. However, the design used a solid impeller, which was run using an external driver and could not be superimposed on current Fontan modifications [22].

The circulation assist device disclosed herein is engineered with the goal of providing venous blood flow assistance to the cavopulmonary connection in the Fontan circulation. The device will be implanted in place of the interposition tube graft conventionally used to achieve the inferior cavopulmonary connection (IVC to the pulmonary artery). Successful augmentation in the IVC will result in lowering of the high central venous pressure and its resultant detrimental congestive effects such as liver fibrosis and cirrhosis and protein losing enteropathy.

Figure 2:
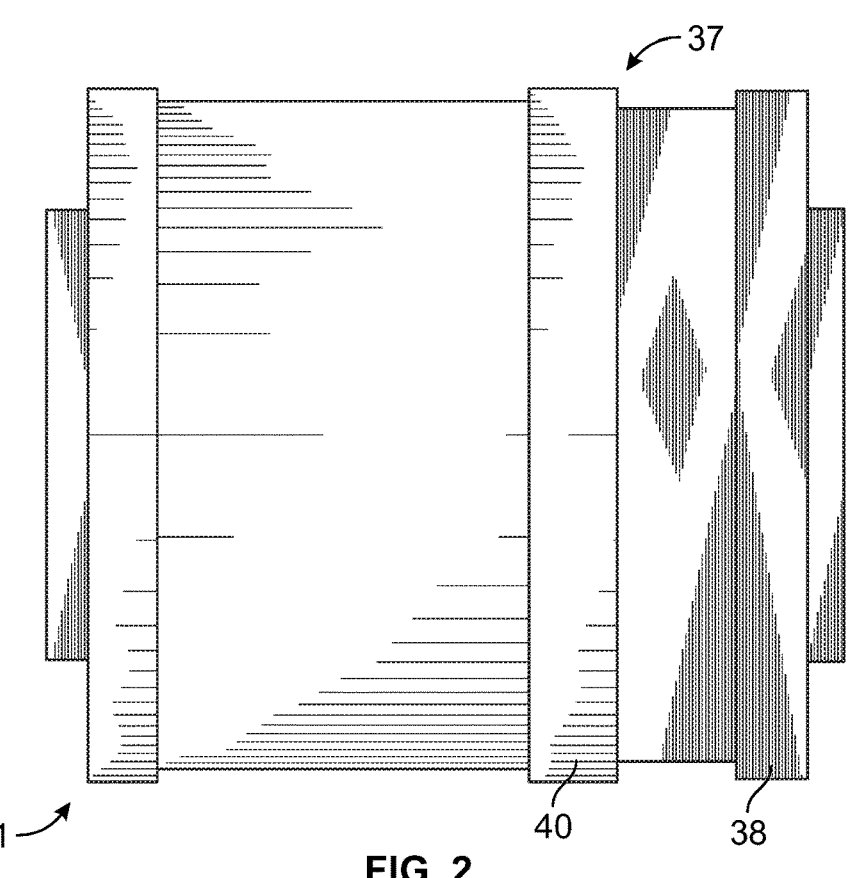
FIG. 2 shows a side view of a fully assembled embodiment of the circulation assist device.

FIG. 1 shows a cross-sectional view of a circulation assist device 1. Fluid enters circulation assist device 1 through inlet 3 and exits through outlet 5. A central longitudinal axis 7 extends between inlet 3 and outlet 5. The circulation assist device 1 further includes a stator 11 and a rotor 9. The stator has at least one stator coil and the rotor has at least one rotor magnet. An impeller 13 is driven by rotation of the rotor 9. All components are enclosed within stator shell 37, as shown in the side view of a fully assembled circulation assist device 1 at FIG. 2. In the illustrated embodiment, the stator shell 37 has an upstream part 38 separate from a downstream part 40. However, it should be understood that the stator shell 37 can have a single part, or more than two parts.

Figure 3:
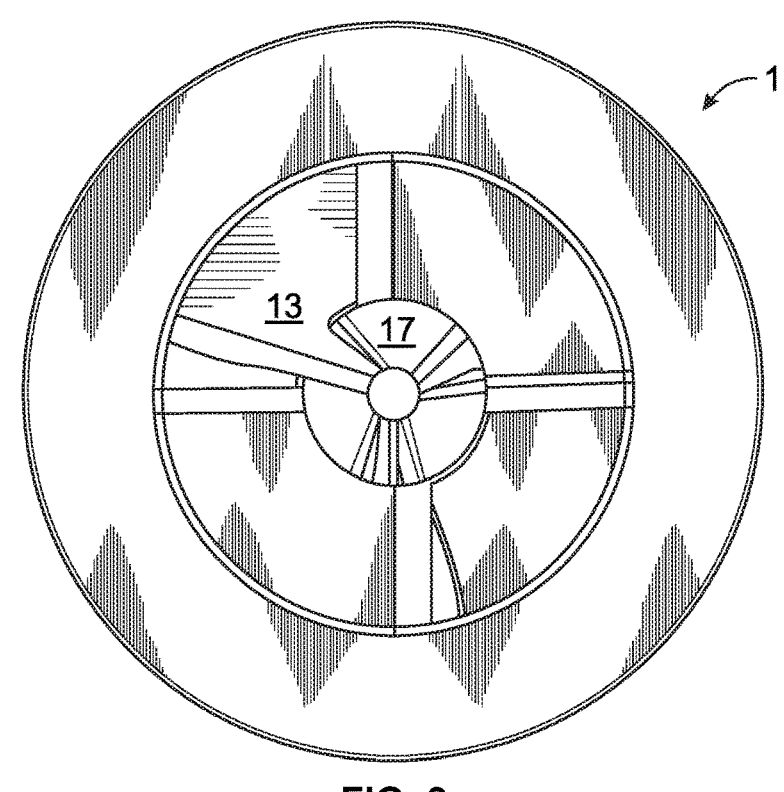
FIG. 3 shows an inlet view of a fully assembled embodiment of the circulation assist device.

As shown in the inlet view of FIG. 3, the impeller 13 at least partially defines a central lumen 17 of the circulation assist device 1. The central lumen 17 extends through the circulation assist device 1 between the inlet 3 and the outlet 5 along the central longitudinal axis 7. Specifically, in the embodiment shown in FIGS. 1-3, the impeller blades 15a, 15b, 15c have radially external sides 19a, 19b, and 19c and radially internal sides 21a, 21b, and 21c. The radially internal sides 21 are radially spaced from a central longitudinal axis 7. At least a portion of the radially internal sides 21 at least partially define the central lumen 17.

The circulation assist device 1, when in operation, will increase flow through the cavopulmonary junction, thereby relieving upstream pressure on the venous system. However, it is important to consider the resistance that the circulation assist device 1 adds to the venous system should the pump ever malfunction. The circulation assist device 1 disclosed herein has the advantage of a very low forward static pressure drop, so that if the impeller stops moving, the resistance is close to what would be expected for a typical Fontan circulation. Generally, the central lumen 17 is open enough to facilitate fluid passage even when the blades 15 are stopped, minimizing the forward static pressure drop through the circulation assist device 1. The forward static pressure drop may be, for example, no greater than about 5 mmHg for flows up to 3 L/min when the impeller is stationary (fluid flow through the Fontan circulation, that is, between the caudal intrapericardial inferior vena cava and the central pulmonary artery, is not typically above 3 L/min). In other embodiments, the forward static pressure drop for flows up to 3 L/min is no greater than 4.5 mmHg, or no greater than 4 mmHg, or no greater than 3.5 mmHg, or no greater than 3 mmHg, or no greater than 2.5 mmHg, or no greater than 2 mmHg, or no greater than 1.5 mmHg, or no greater than 1 mmHg, or no greater than 0.5 mmHg.

The pulmonary pressure rise when the circulation assist device 1 is in operation is designed so as not to overload the pulmonary vascular bed but to provide sufficient flow and to enhance gas exchange and blood oxygenation in the pulmonary capillaries. The forward pressure rise can be from about 1 mmHg to about 35 mmHg, and is preferably greater than 10 mmHg when the impeller is rotating. For example, at flows up to 4 L/min, the forward pressure rise is less than 30-35 mmHg, which, unlike adult LVADs and some pediatric LVADs, should not cause a significant concern of pulmonary hypertension.

Figure 4:
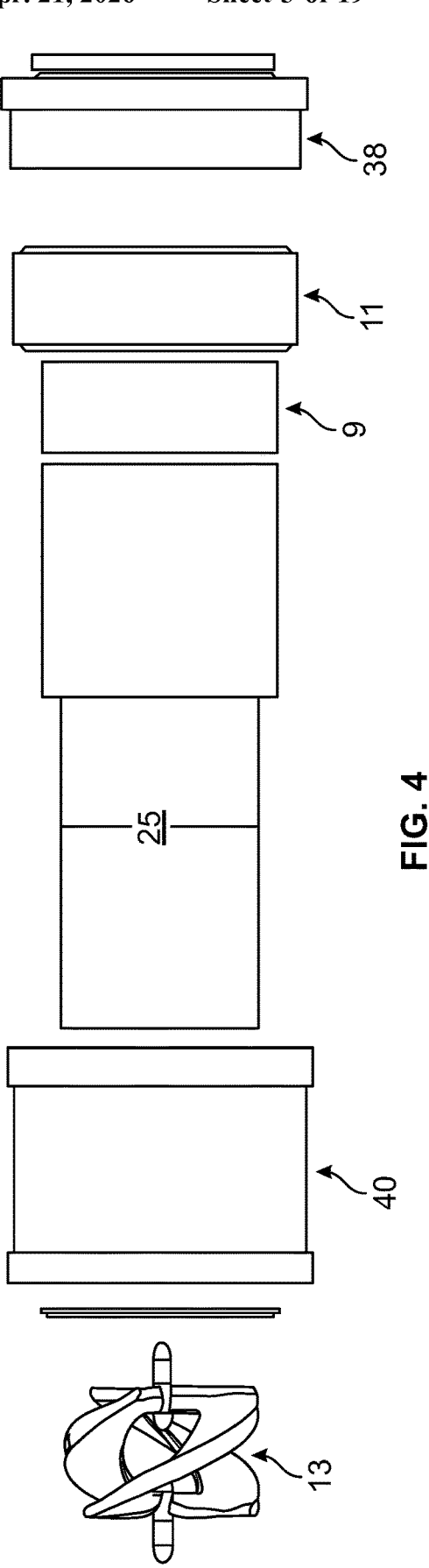
FIG. 4 shows an exploded view of the circulation assist device.
Figure 5:
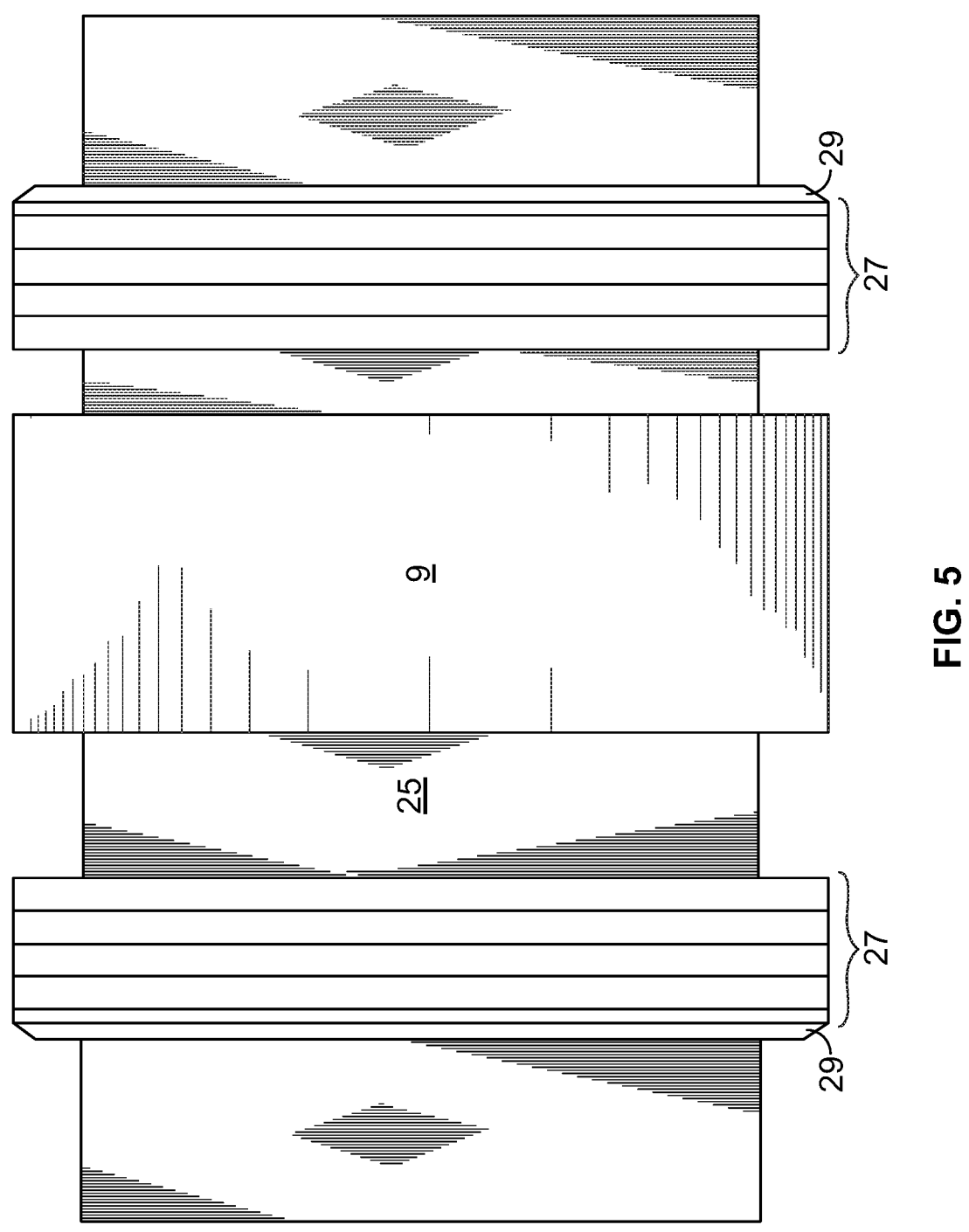
FIG. 5 shows a side view of a partially assembled embodiment of the circulation assist device.
Figure 6:
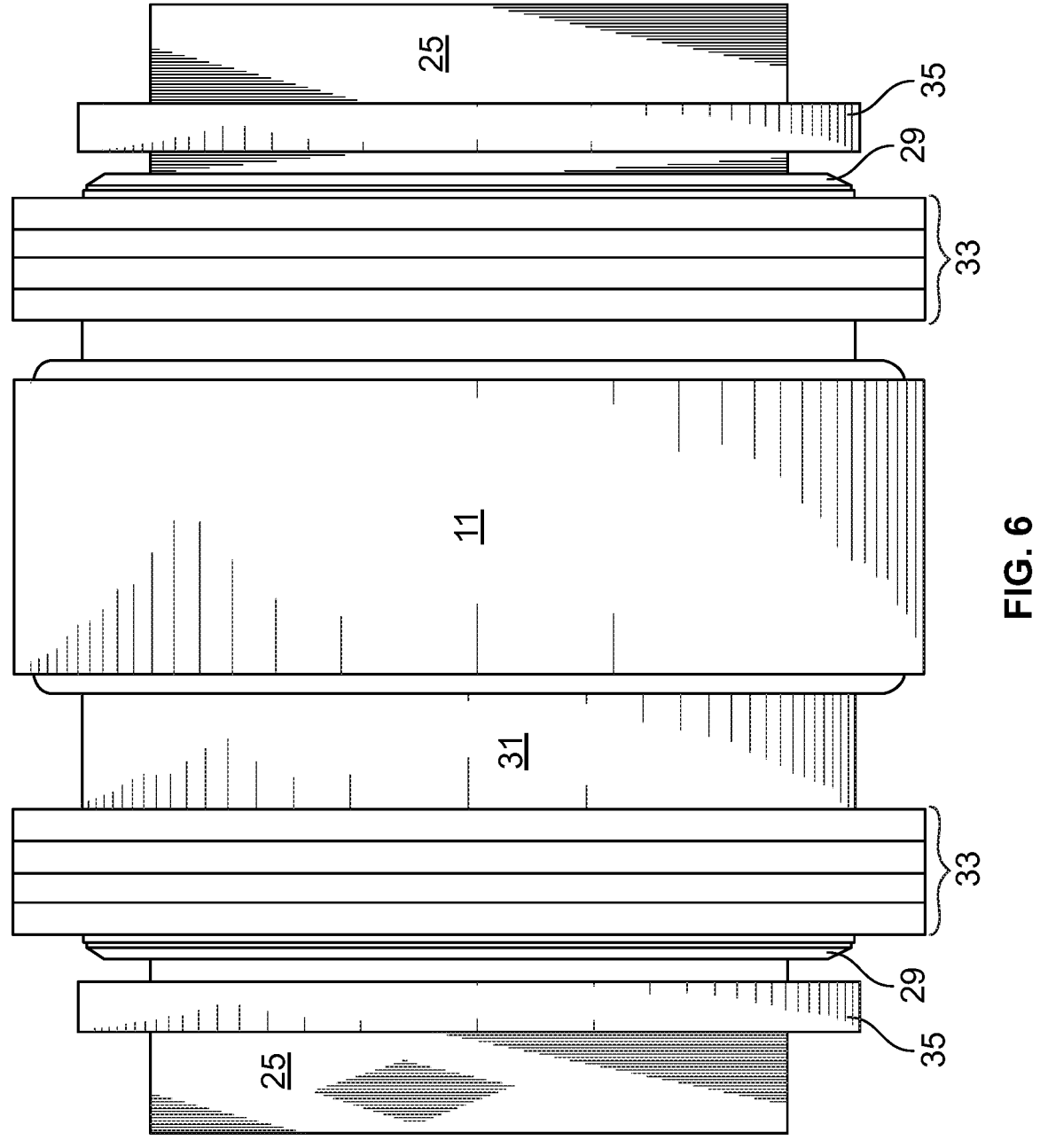
FIG. 6 shows a side view of a partially assembled embodiment of the circulation assist device.

FIG. 4 shows an exploded view of some major components of an example circulation assist device 1 (rotor magnetic bearings and stator magnetic bearings are hidden from this view so that other major components can be clearly illustrated). As also shown in the cross section of FIG. 1, in this embodiment, impeller 13 is positioned radially inward from impeller housing 25. Stationary impeller housing 25 is positioned radially inward from rotor 9 and rotor components, whereas rotor 9 and rotor components are positioned radially inward from stator 11 and stator components. FIG. 5 shows a side view of the impeller housing 25, which is surrounded by the rotor 9, rotor magnetic bearings 27, and rotor axial thrust runner/stop component/bearing 29 (rotor shell, stator and stator components are hidden in FIG. 5). FIG. 6 shows a side view of the circulation assist device 1 with the stator shell hidden. As shown in FIG. 6, the rotor shell 31, which rotates with the rotor, is positioned radially inward from the stator 11, the stator magnetic bearings 33, and the stator axial thrust runner/stop component/bearing 35. In some embodiments, the functions of the rotor and the impeller can be integrated into a single component.

The rotor magnetic bearings 27, shown in FIG. 5, form radial magnetic bearings with the corresponding stator magnetic bearings 33, which are shown in FIG. 6. Stator magnetic bearings 33 are attached to stationary stator shell 31. Eight rotor/stator magnet pairings are shown in the embodiment of FIG. 5. However, in other embodiments, different numbers of rotor/stator magnetic bearing pairings are possible. The radial magnetic bearing offset produces a very low load approximating axial thrust of the operating impeller, but in the opposite direction (such as described in U.S. Pat. Nos. 8,992,407 and 8,177,703, which are incorporated by reference). Alternatively, non-magnetic bearings could also be employed.

Electrical activation of the coils within stator 11 induce rotation of rotor 9, which in turn causes rotation of the rotor shell 31, the rotor magnetic bearings 27, and the rotor axial thrust runner/stop component/bearing 29.

Rotor axial thrust stop component/bearing 29, shown in FIGS. 5 and 6, is axially adjustable. Axial contacts are very near zero force when the pump is running, with residual magnetic force subtracting from hydraulic thrust applied to the front stop. The longitudinal positioning of the rotating and stationary thrust stop components 29, 35 can be switched, in some embodiments.

Figure 7:
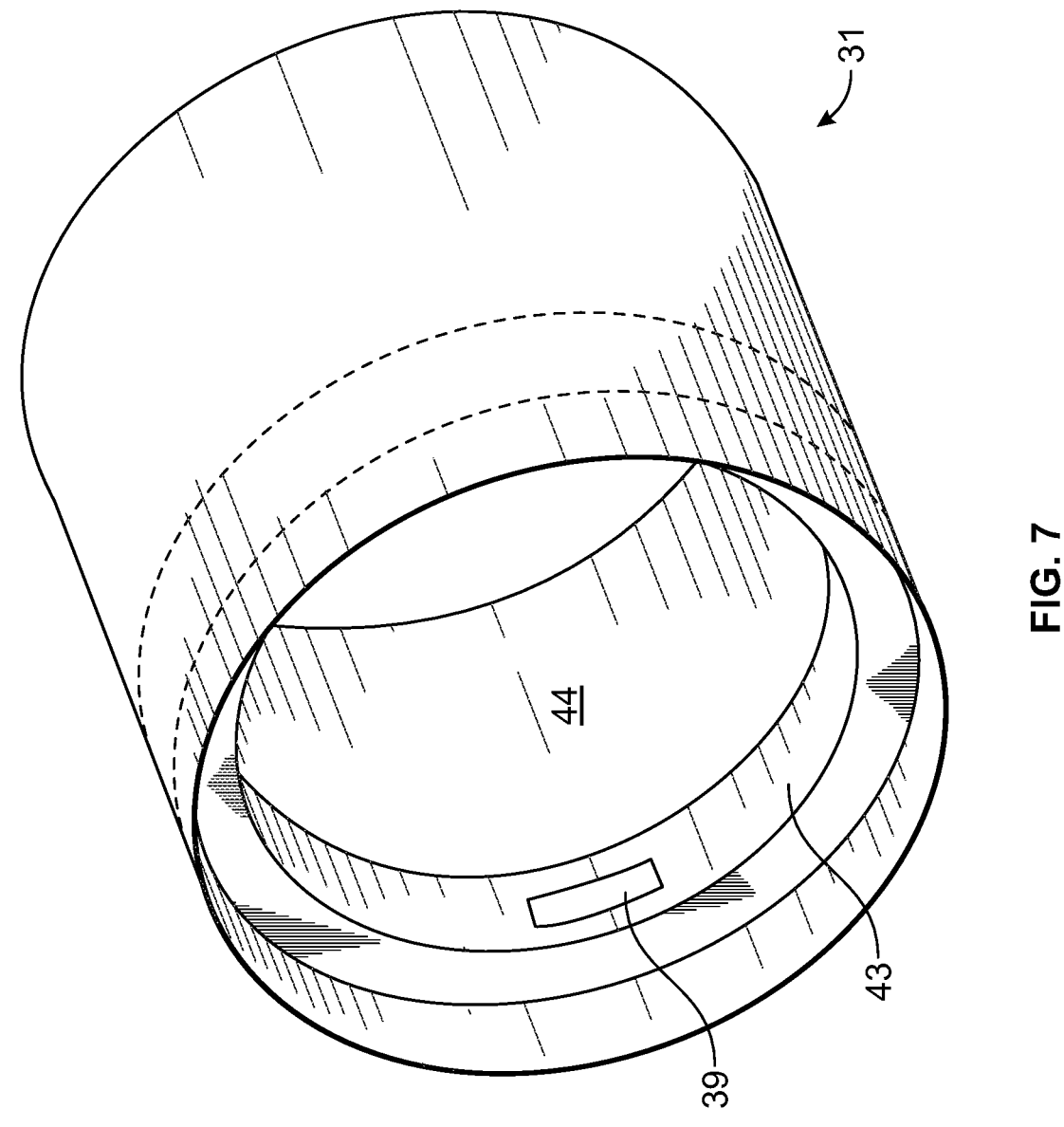
FIG. 7 shows a perspective view of a rotor shell embodiment.
Figure 8:
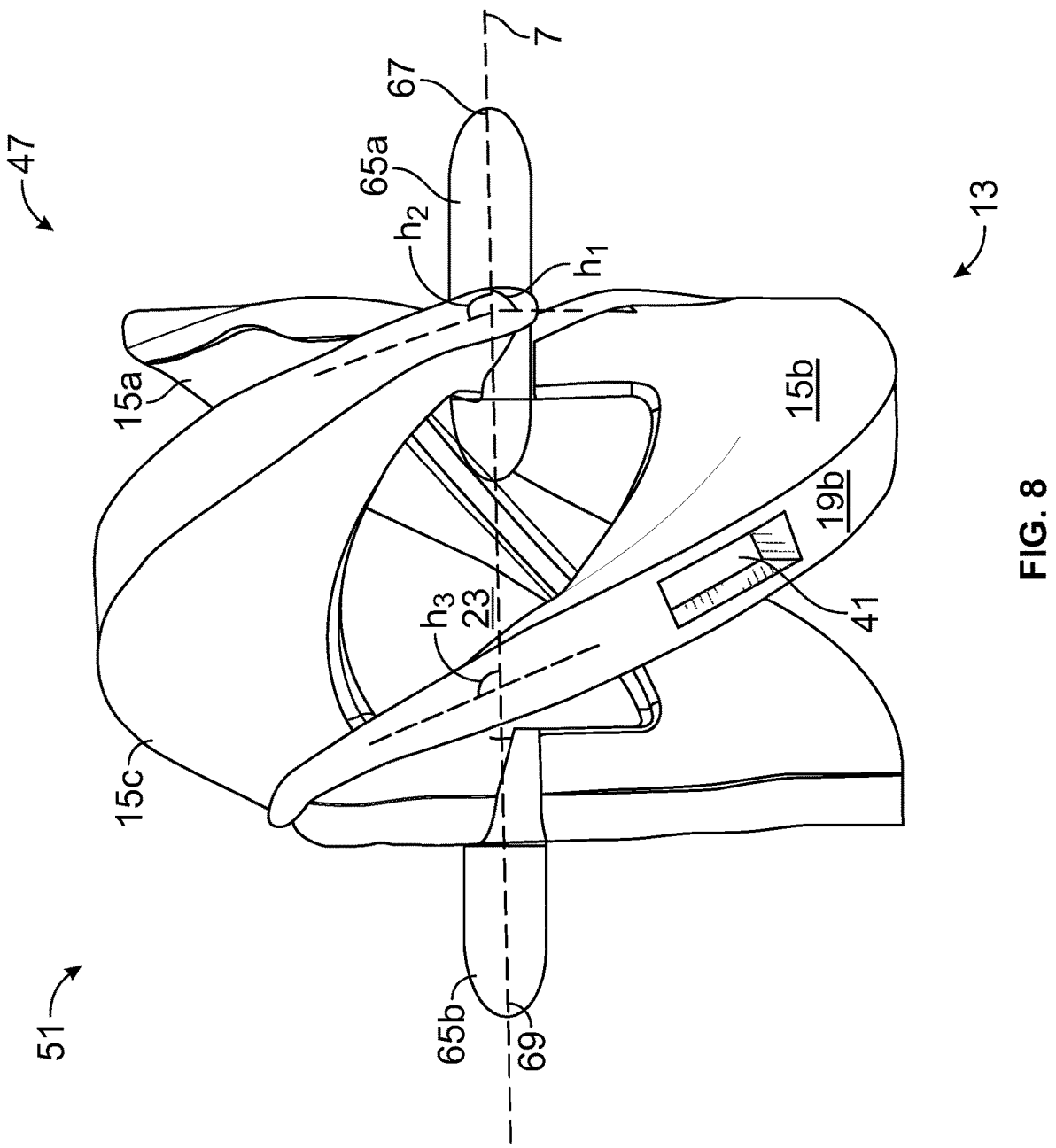
FIG. 8 shows a side view of an impeller embodiment.

A perspective view of the rotor shell 31 is shown in FIG. 7, and a side view of the impeller 13 is shown in FIG. 8. Rotor 9 (not shown) is coupled to the rotor shell 31 at a position longitudinally spaced from a drive magnet 39.

Drive magnet 39 magnetically couples with a driven magnet 41 positioned on a radially external side 19b of an impeller blade 15b. In this way, rotation of the rotor results in synchronized rotation of the impeller. This serves as an axial magnetic bearing for the pump rotor to offset a hydraulic thrust on the impeller. While a single drive/driven magnet pairing is illustrated, it should be understood that multiple drive/driven magnet pairings are within the scope of this disclosure.

Drive magnet 39 is positioned on a ring 43 that extends inwardly from an inner surface 44 of the rotor shell 31 to bridge the gap necessitated by the thickness of the rotor and rotor components. Still, the driven magnet 41 on the rotor shell 31 is slightly radially offset from the drive magnet 39 on the impeller blade 15 (refer also to FIG. 1). In the embodiment shown, the radially oriented magnetic attraction between drive and driven magnets 39, 41 extends through the non-rotating impeller housing 25, such that the rotor and stator parts are sealed from fluid flow. In this way, the wall of impeller housing 25 is a sealing wall 43 configured to isolate blood traveling through the central lumen from the rotor and the stator.

Figure 10:
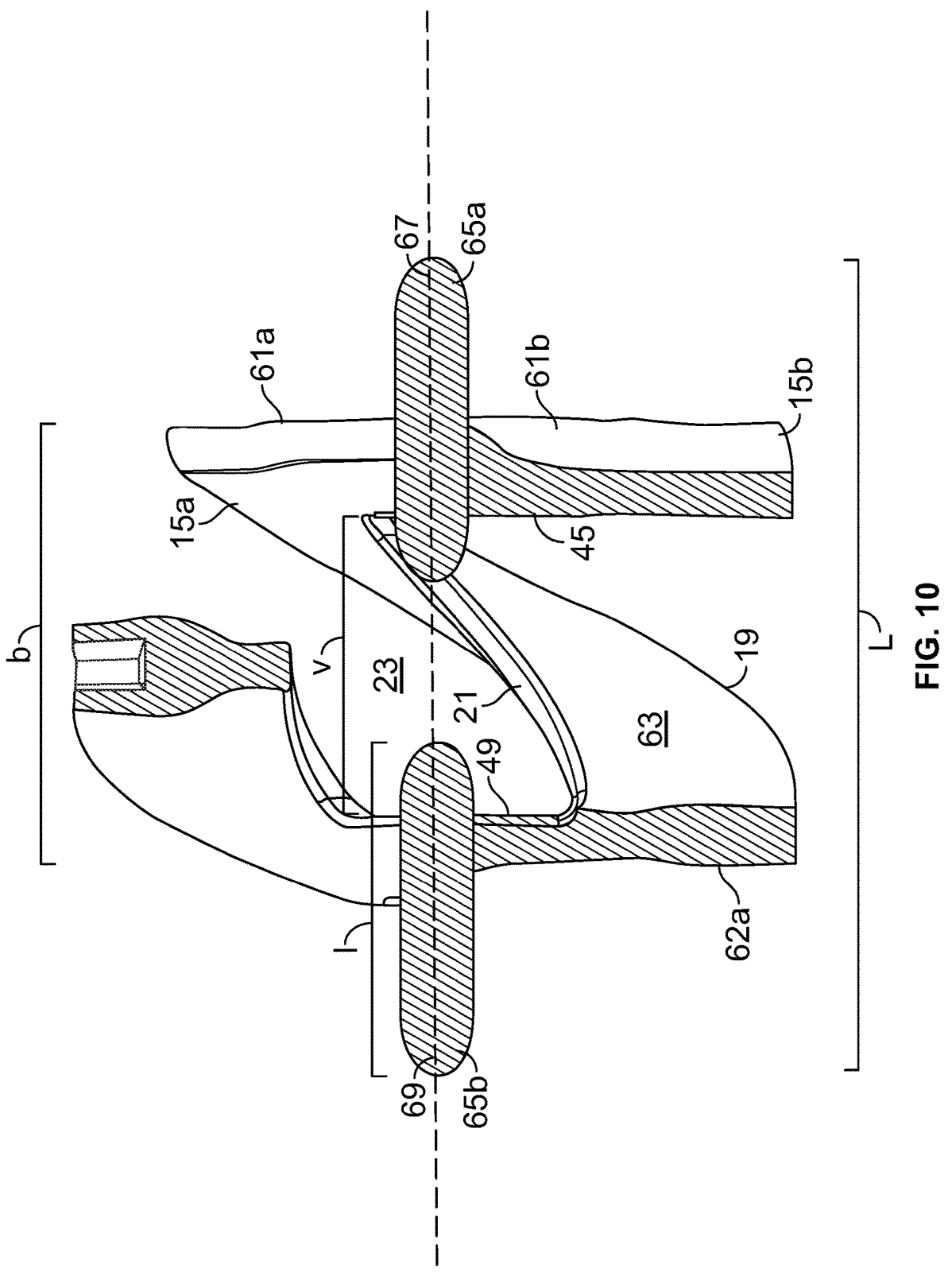
FIG. 10 shows a longitudinal cross-sectional view of an impeller embodiment.

FIG. 8 shows a side view of an example impeller 13. In this embodiment, three impeller blades 15a, 15b, 15c extend helically around an axially extending void 23 that is part of the larger central lumen 17 of the circulation assist device 1. The number of impeller blades can vary. For example, the embodiment shown in FIG. 11 has three impeller blades 15a, 15b, and 15c. However, this is not meant to be limiting. In other embodiments, the impeller can have a single blade, two blades, four blades, five blades, six blades, seven blades, or more. As seen in FIG. 10, the axially extending void 23 (which is coaxial with the central longitudinal axis 7) is entirely devoid of structure to reduce the forward static pressure drop. The axially extending void 23 extends a length v along the longitudinal axis 7 between a downstream edge 45 of the leading portion 47 of the blades 15 and an upstream edge 49 of the trailing portion 51 of the blades 15. In some embodiments, the axially extending void length v can be a fraction of the full length b of an impeller blade 15, with b being measured from an upstream-most leading edge 61a to a downstream-most trailing edge 62a of a blade. The ratio v/b can range from about 0.5 to about 1, including 0.5, 0.55, 0.6, 0.65, 0.7, 0.75, 0.8, 0.85, 0.9, 0.95, and 1.

Figure 9:
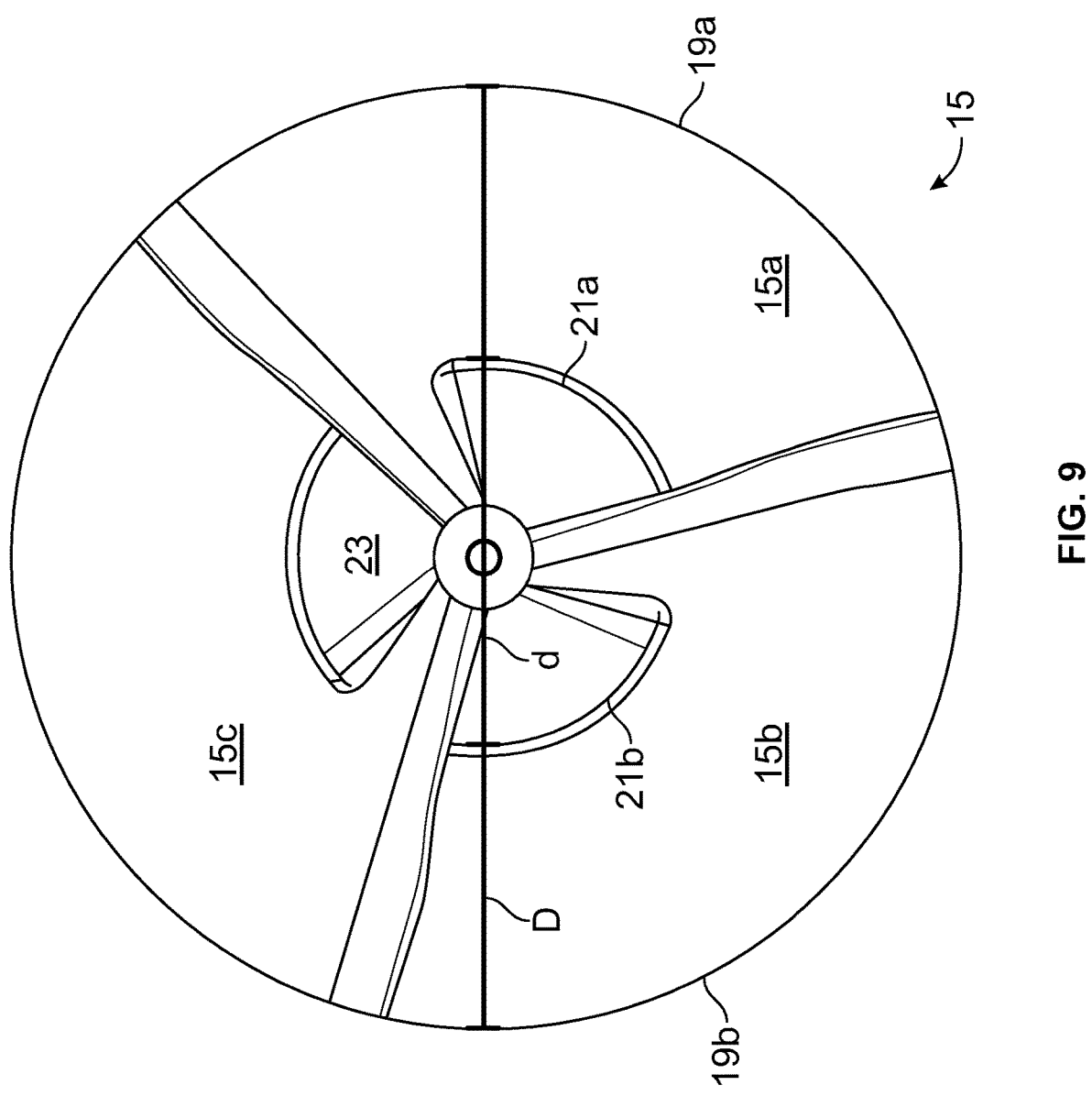
FIG. 9 shows a view of an impeller from the inlet of an embodiment of the circulation assist device.

A front view of the impeller 15 is shown in FIG. 9. The axially extending void 23 can have a diameter d as measured between a first radially internal edge 21a of an impeller blade 15a and a second radially internal edge 21b of a second impeller blade 15b positioned opposite the central longitudinal axis 7. In some embodiments, the axially extending void diameter d can be a fraction of the full diameter D of the impeller 13, D being measured between a first radially external edge 19a of an impeller blade 15a and a second radially external edge 19b of a second impeller blade 15b positioned opposite the central longitudinal axis 7. The ratio d/D can range, for example from about 0.3 to about 0.8, including 0.3, 0.4, 0.5, 0.6, 0.7, or 0.8.

Referring again to FIG. 10, the impeller blades 15 are shaped such that the tip velocity approximates the laminar inlet velocity profile and to smoothly accelerate blood traveling between the inlet and the outlet. The leading edge 61 of an impeller blade 15 has a varying attack angle relative to the central longitudinal axis 7, such that the blade velocity varies with radius to approximate the laminar velocity profile of entering fluid. Said another way, an attack angle formed between an upstream surface 63 of an impeller blade 15 and the central longitudinal axis 7 varies moving radially outward from the radially internal edge 21 of the blade 15. That is, attack angles measured at the root (the portion of the blade closest to the longitudinal axis) may be different than attack angles measured closer to the radially external edge of the blade.

As shown in FIG. 8, a helix angle of the rotatable impeller blade varies along the longitudinal axis. For example, a first helix angle $h_1$ is different from a second helix angle $h_2$ (longitudinally spaced from $h_1$) which is different from helix angle $h_3$ (which is longitudinally spaced from $h_1$ and $h_2$).

Figure 11:
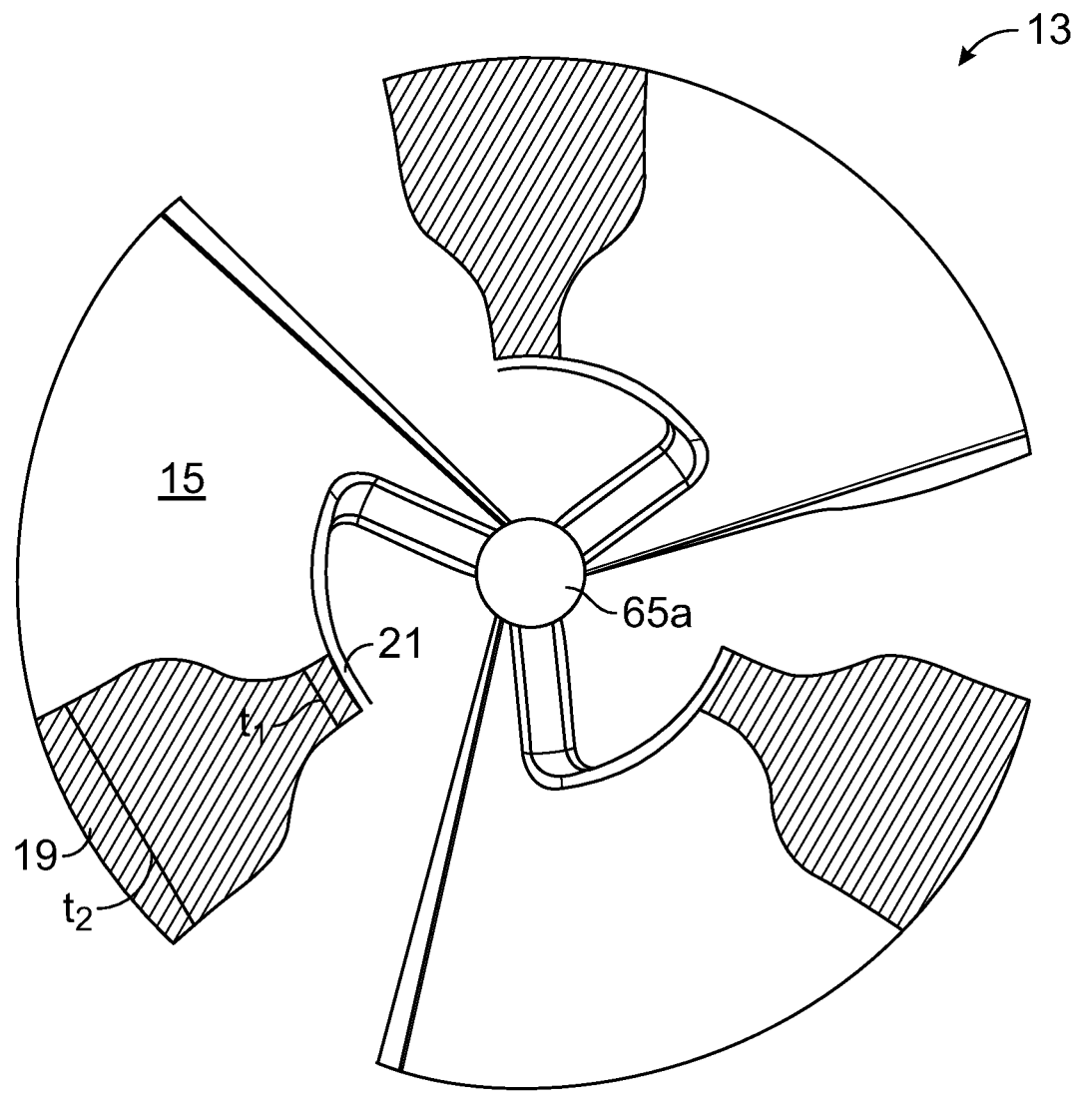
FIG. 11 shows a transverse cross-sectional view of an impeller embodiment.

Finally, as shown in FIG. 11, the thickness t of the rotatable impeller blade increases moving radially outward, leaving more space in the center of the impeller 13 to facilitate fluid flow therethrough ($t_1$ near the radially internal edge 21 is less than $t_2$ near the radially external edge 19).

The impeller embodiment shown in FIGS. 8-11 optionally includes upstream and downstream axles 65a, 65b. The axles are coupled to the impeller blades 15 and extend partially along the longitudinal axis 7. In the illustrated embodiment, the impeller blades 15 are coupled to the upstream axle 65a, bridge the axially extending void 23, and are coupled to the downstream axle 65b. The axles rotate along with the impeller blades 15, being driven by driven magnet 41. As shown in FIG. 10, axially extending void 23 longitudinally separates the upstream and downstream axles 65a, 65b, such that neither axle extends the full length L of impeller 13 (L being measured from the upstream most point 67 on the upstream axle 65a to the downstream most point 69 on the downstream axle 65b, see FIG. 10). That is, the length l of each axle 65a, 65b along the longitudinal axis is shorter than the total length of the impeller L. It is noted that the illustrated embodiment has two axles, but alternate approaches to the impeller axial and radial bearings could eliminate either or both axles.

Figure 12:
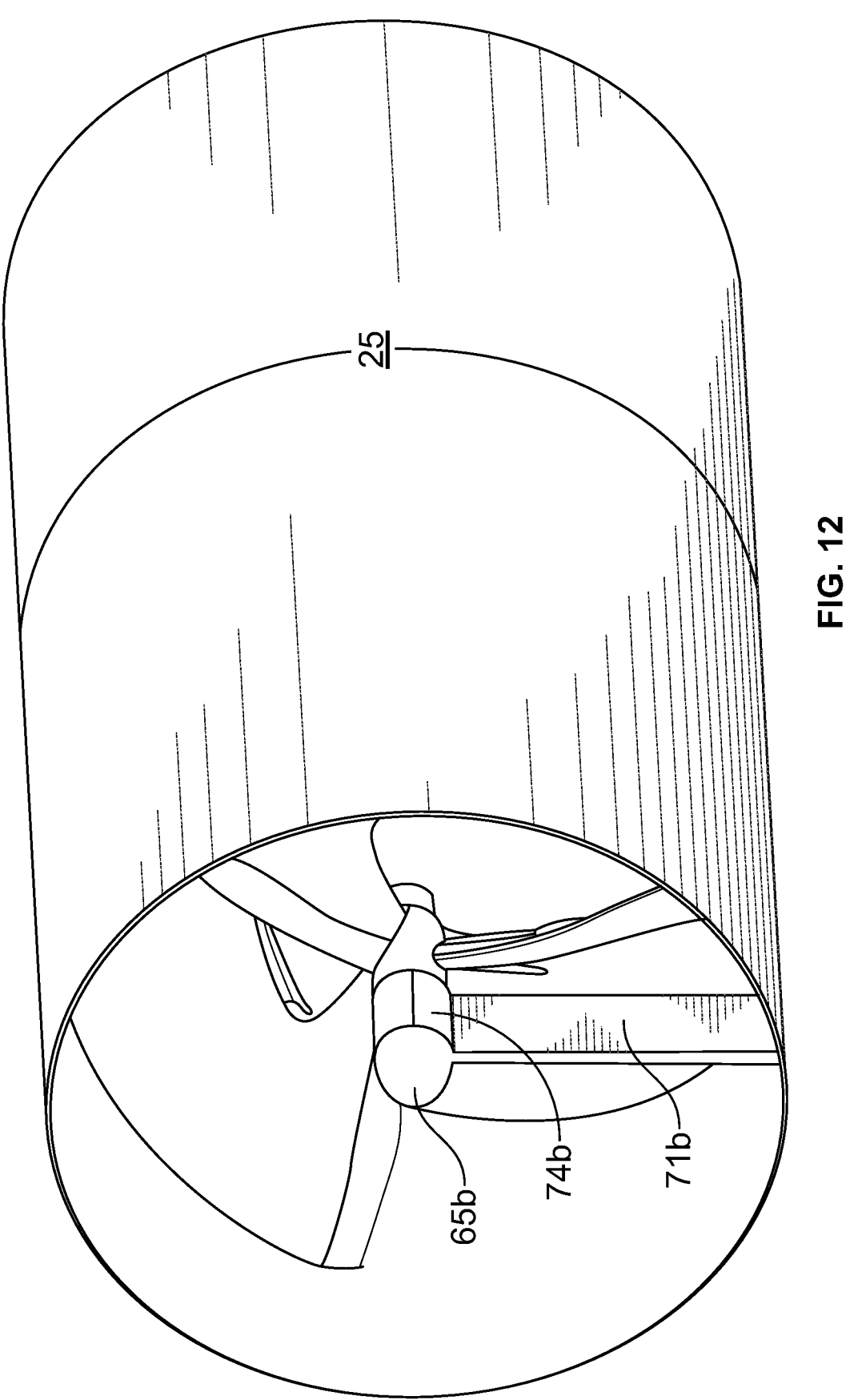
FIG. 12 shows a perspective view of an impeller seated within an impeller housing in an example embodiment of the circulation assist device.
Figure 13:
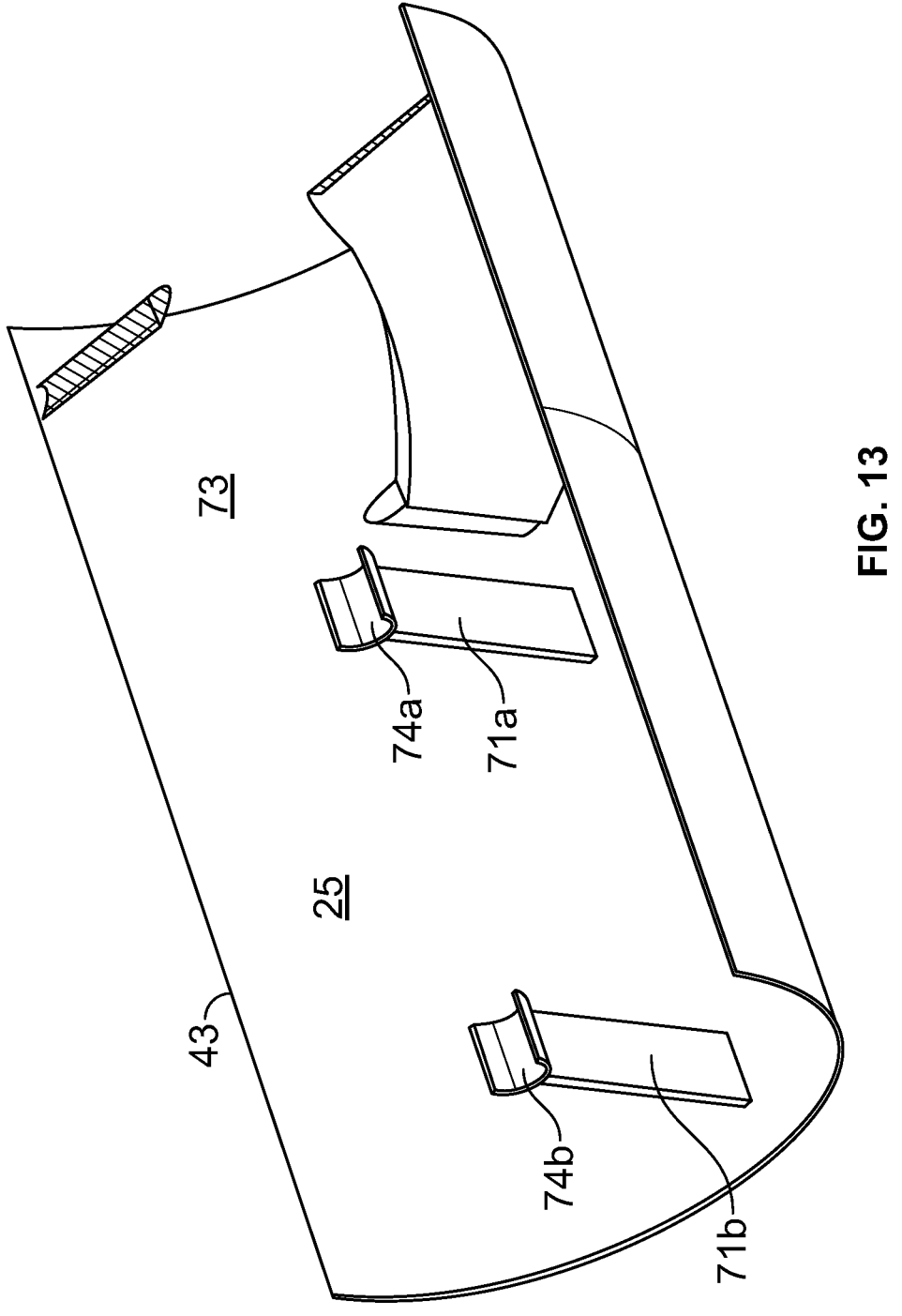
FIG. 13 shows a longitudinal cross-sectional view of an impeller housing embodiment.

FIG. 12 is a perspective view of the outlet side of an impeller housing 25 with impeller 13 seated therein. A downstream axle support 71b is visible supporting downstream axle 65b. Upstream and downstream axles 65a, 65b are radially supported by upstream and downstream axle supports 71a, 71b, both of which are shown in the cross-sectional perspective view of impeller housing at FIG. 13. Axle supports 71 are coupled to and extend radially inward from an inner surface 73 of the stationary impeller housing 25, and stabilize the impeller axles 65 along the longitudinal axis 7 using hydrodynamic bearings 74a, 74b. In the embodiment illustrated in FIG. 12, the axle support bearings 74 extend at least partially around the axle 65b in a circumferential direction. The open construction of the axle support bearings provides a well-washed flow path with limited blood cell dwell in a shear zone, thereby minimizing risk of deposition or hemolysis. The axle supports can optionally provide axial thrust stops in cooperation with the axles.

Figure 14:
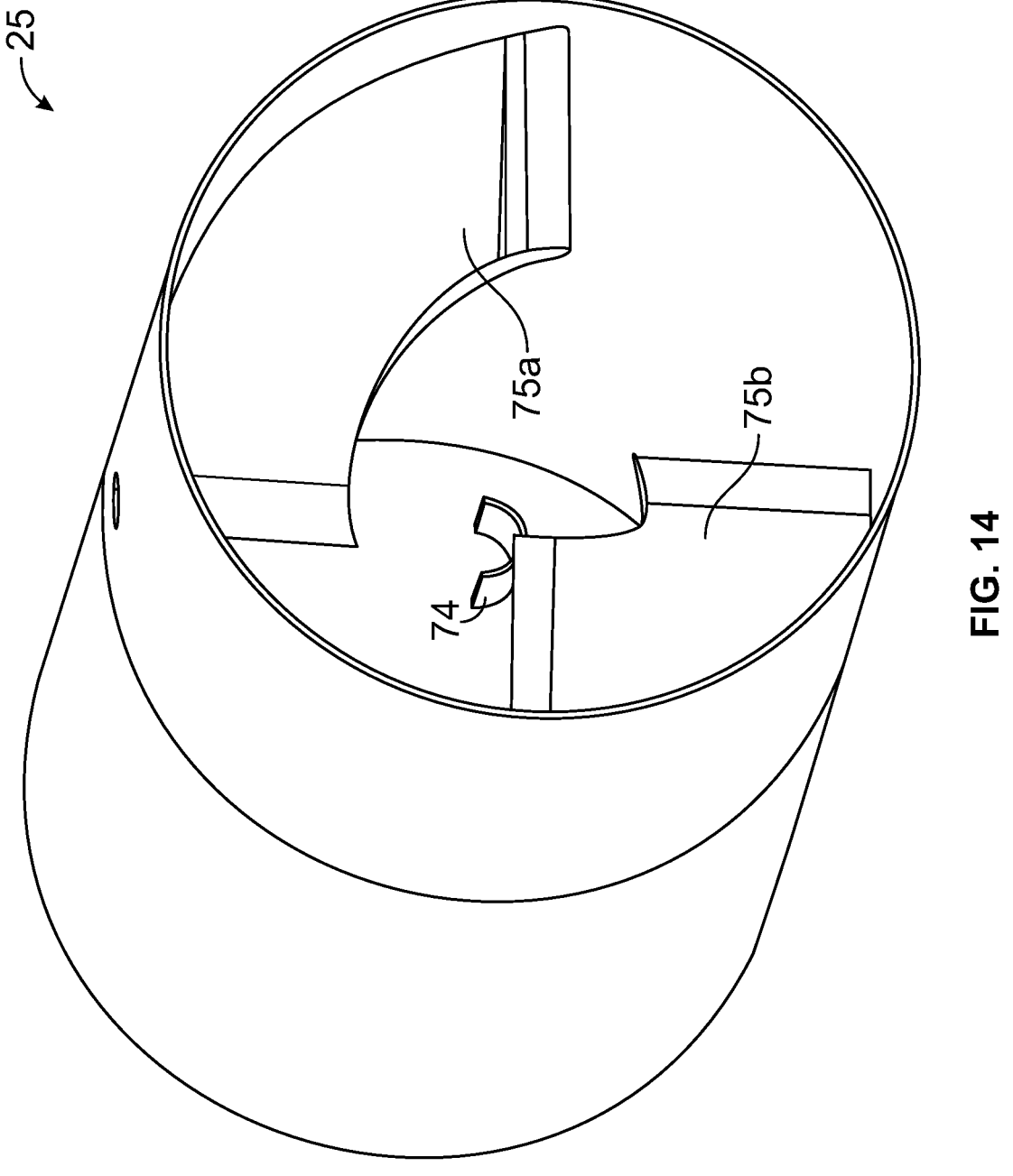
FIG. 14 shows a perspective view of the inlet side of an impeller housing embodiment.

FIG. 14 shows a perspective view of impeller housing 25 looking into the inlet 3. In addition to the aforementioned axle supports 71, stationary impeller housing 25 can include one or more stationary inlet guide vanes and one or more stationary outlet guide vanes. Two inlet guide vanes 75a, 75b meet incoming blood and resist pre-rotation prior to the flow meeting the impeller 13. This aids pump performance.

Figure 15A:
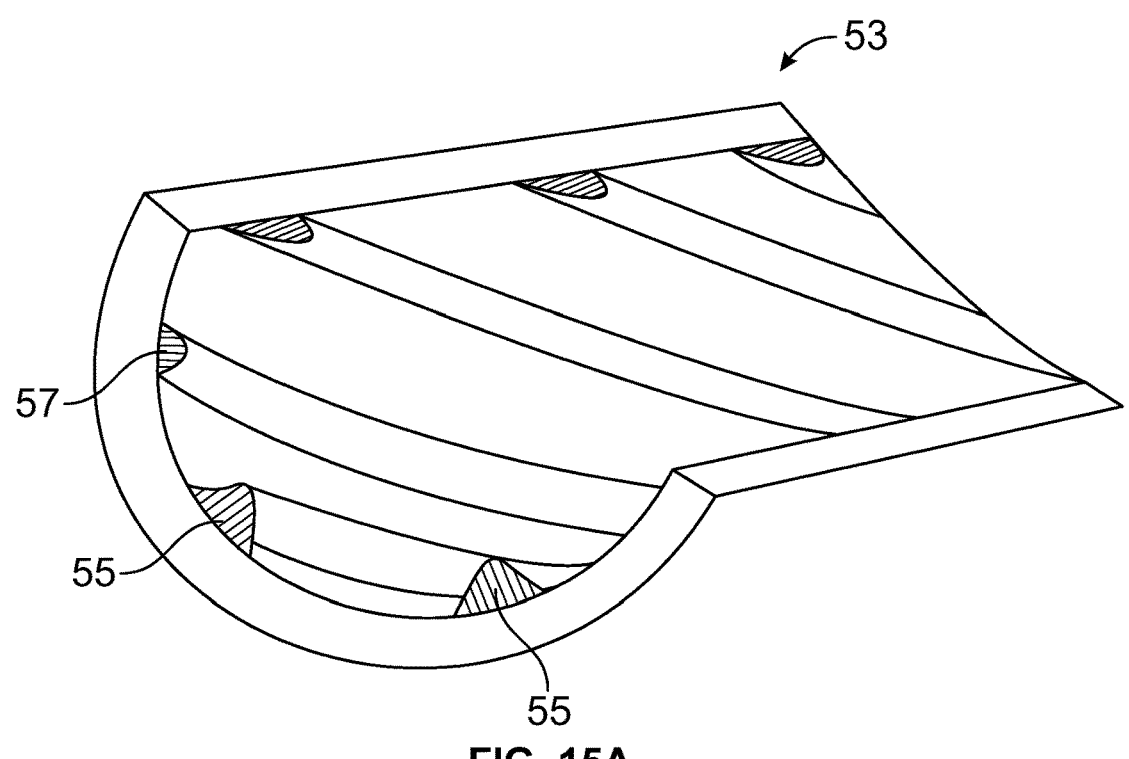
FIG. 15A shows a partial cross-sectional, perspective view of an impeller embodiment.
Figure 15B:
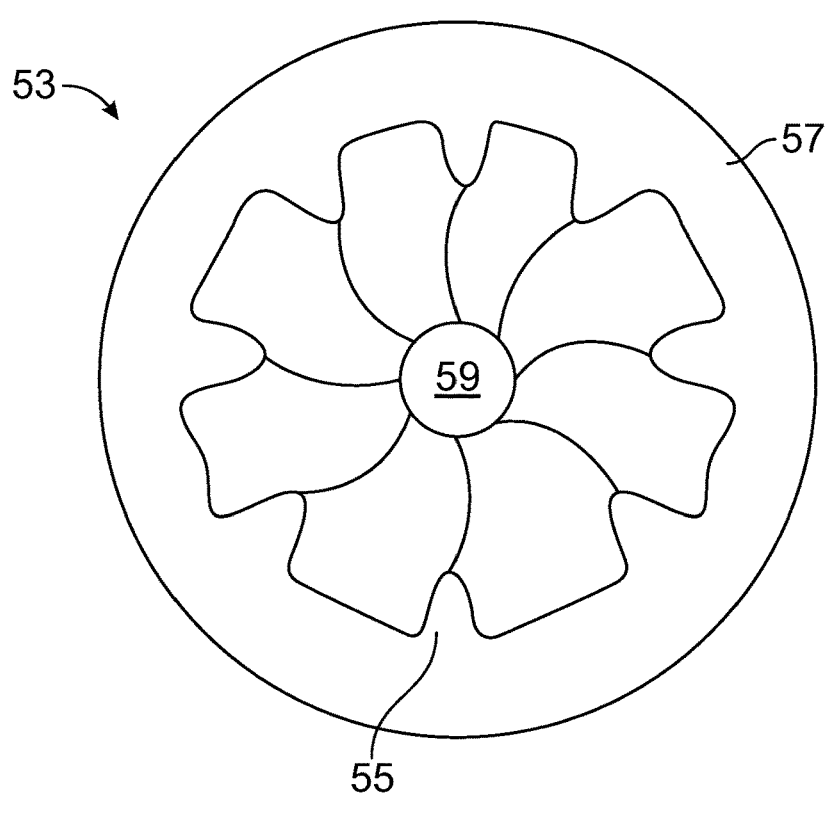
FIG. 15B shows an inlet view of an impeller embodiment.

Other impeller embodiments can have alternative configurations to facilitate passage of fluid regardless of whether the impeller is actively rotating. For example, FIG. 15A shows a perspective, partial cross-sectional view of an impeller 53. FIG. 15B shows a front view of impeller 53. Impeller 53 includes blades 55 that extend inward from an inner surface of a rotating shell 57, such that a large axially extending void 59 travels the full length L of the impeller 53, with L measured from the upstream edge to the downstream edge of the impeller (v/b=1). In this embodiment, no axles are required to rotate the impeller.

Materials are selected to minimize thrombosis. In one embodiment, any or all parts of the circulation assist device can be coated with a low drag, high blood compatibility coating. For example, a hard PTFE copolymer, which has demonstrated hydrophobic and oliophobic properties can be applied to any or all blood contacting surfaces. This has many virtues; (1) a hard, wear resistant, low friction surface for the bearings; (2) a low drag surface for the pump, reducing static pressure drop, (3) potentially high blood compatibility due to the hydrophobicity and inertness of the PTFE. Other types of materials may also be selected to minimize thrombosis, and may be used as coatings or components of the circulation assist device may be formed fully of the non-thrombogenic material.

Figure 16:
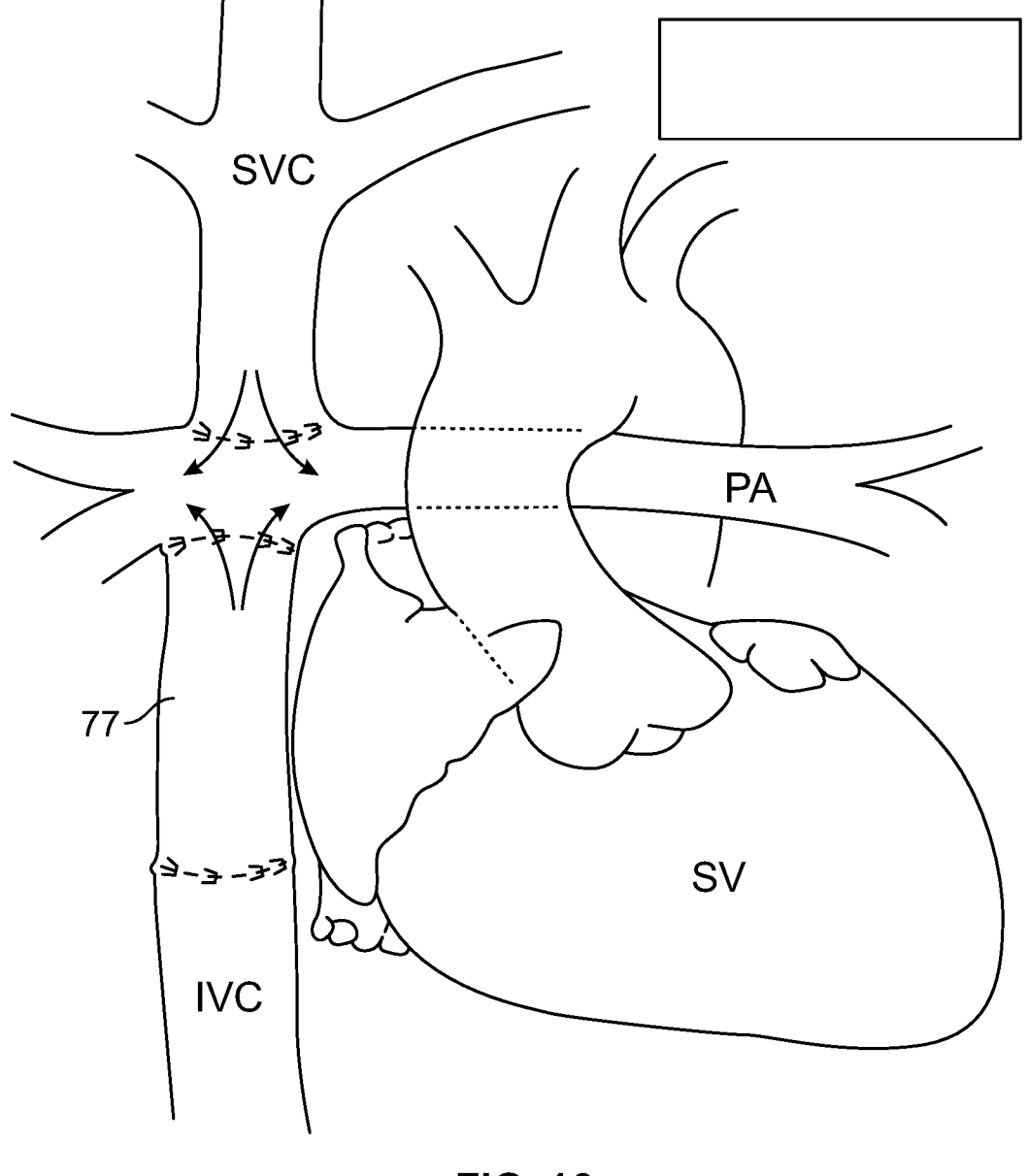
FIG. 16 is a diagram of the conventional Fontan circulation.

The circulation assist devices disclosed herein can be used to decrease systemic venous pressure in the Fontan circulation. FIG. 16 shows a diagram of a conventional Fontan circulation path in a single ventricle (SV) patient. A graft 77 connects the inferior vena cava (IVC) with the pulmonary artery (PA), and the SV is solely responsible for moving the blood through the pulmonary and systemic vasculature. At the juncture of the IVC and PA, the slow moving blood creates a pressure buildup that can ultimately cause end-organ failure, as discussed above.

The circulation assist devices disclosed herein can be used instead of, or as a replacement for, interposition graft 77 to provide additional pumping support to the SV circulation, easing pressure in the systemic venous system. The circulation assist devices can be used to support single ventricle patients right from Fontan conversion to allow single ventricle patients to have as close to a biventricular physiology as possible and prevent any changes secondary to venous congestion. In patients with an already present deficiency in the Fontan circulation, the existing interposition graft 77 can be replaced with the proposed circulation assist device to provide long term mechanical assistance.

Figure 17:
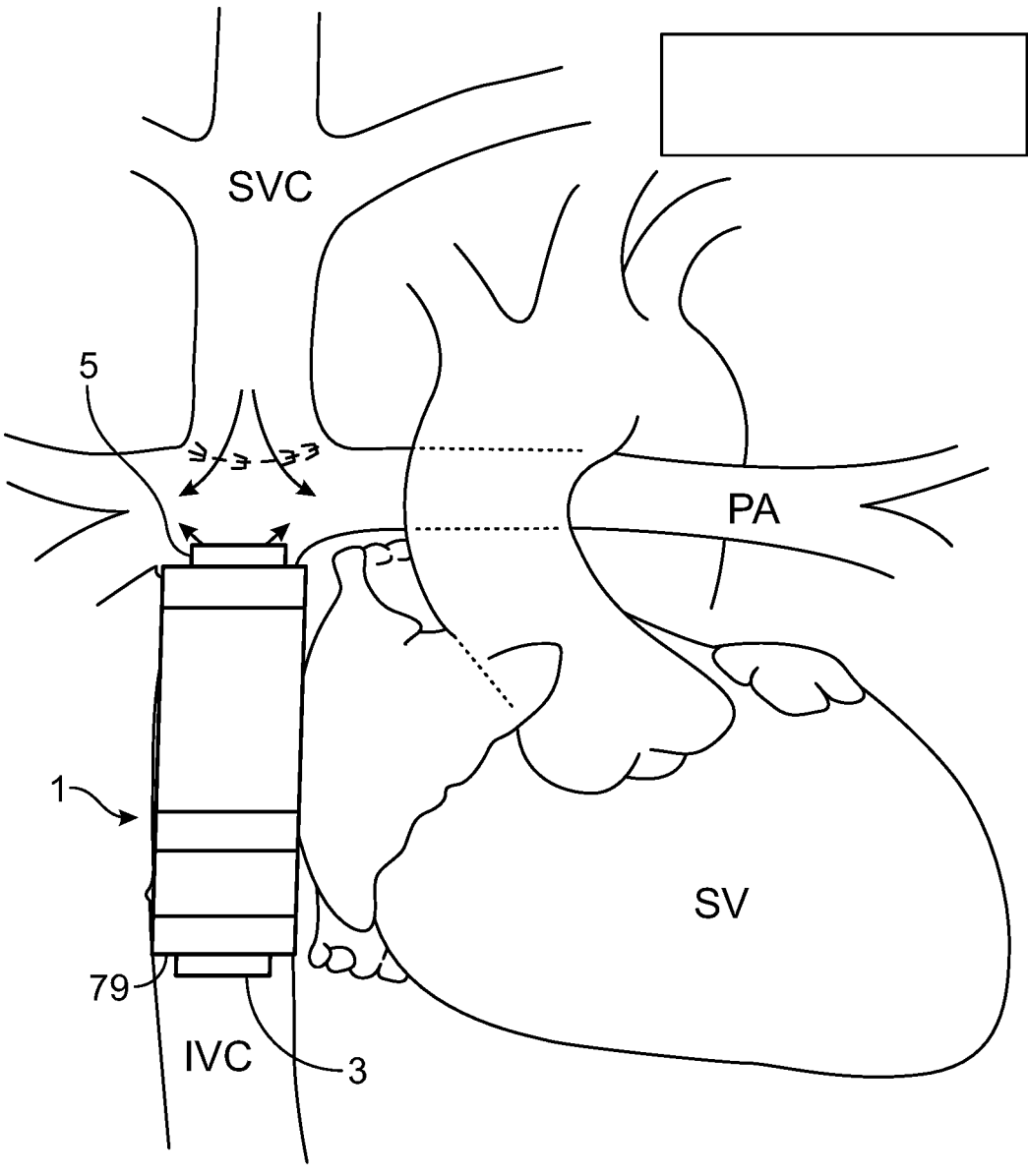
FIG. 17 is a diagram of the Fontan circulation including an embodiment of the circulation assist device.

The method of decreasing venous pressure, partially depicted in FIG. 17, includes establishing a first fluidic coupling between the caudal intrapericardial inferior vena cava 79 and an inlet 3 of a circulation assist device 1, establishing a second fluidic coupling between the central pulmonary artery and an outlet 5 of the circulation assist device 1, moving blood through the inlet 3 of the circulation assist device 1 at an inlet velocity and an inlet pressure, moving blood through a central lumen of the circulation assist device, rotating at least one rotatable impeller blade to increase blood velocity through the central lumen, and moving blood through the outlet at an outlet velocity and an outlet pressure.

When circulation assist device 1 is in operation, the outlet pressure (downstream) is higher than the inlet pressure (upstream). Impeller speed ranges between 2000 to 5000 RPM in the current execution. It should be apparent to those versed in the art that this pump may be executed in larger or smaller versions. Large versions may run at slower speeds, smaller versions may run at higher speeds to maintain the fundamental flow requirements as set by clinical demands. Speed range can be adapted to the needs of the patient. For example, the outlet pressure can be higher than the inlet pressure by greater than 10 mmHg for pump induced forward flow equal or greater than 3 L/min. When the impeller is stationary, the forward static pressure drop between the inlet and the outlet is minimized. For example, the forward static pressure drop may, in some embodiments, be no greater than 5 mmHg for flows up to 3 L/min when the impeller is stationary (including no greater than 4.5 mmHg, no greater than 4 mmHg, no greater than 3.5 mmHg, no greater than 3 mmHg, no greater than 2.5 mmHg, no greater than 2 mmHg, or greater than 1.5 mmHg, no greater than 1 mmHg, and no greater than 0.5 mmHg).

As described above, the circulation assist device in some embodiments includes an impeller having an axially extending void. The methods disclosed herein include moving blood through an axially extending void, that is entirely devoid of physical structure. The methods can also include moving blood past at least one stationary inlet guide vane and one stationary outlet guide vane. In some embodiments of the methods, an additional circulation assist device may be utilized to replace a segment of the superior vena cava (SVC) approaching the pulmonary artery (PA).

In some embodiments of the methods, the stator coils within the stator of the circulation assist device are activated by electricity. The electrified coils produce a magnetic force that causes rotation of the rotor component. The electricity can be provided by a power source, which can include a battery. The power source can be external to the patient's body, or implantable within the patient's body.

The patient can be a human being, particularly a pediatric human being. As such, the circulation assist device can be sized to fit within the vasculature of a pediatric human being. For example, the full length of the circulation assist device can be (from inlet to outlet) less than 3 centimeters. Should additional length be necessary, in some embodiments, vascular grafts can be interposed on the inlet end, the outlet end, or both (and can be trimmed and tailored during the procedure to customize to patient needs). The diameter, measured between opposing outer surfaces of the circulation assist device, can be less than 35 millimeters. However, in other embodiments, the circulation assist device can be sized and adapted to function in the circulation of any human or non-human animal patient, particularly any patient that can benefit from the relief of heightened systemic venous pressure resulting from surgical procedures such as, but not limited to, the Fontan procedure.

EXAMPLE

The single ventricle Fontan circulation presents special challenges in providing mechanical circulatory support effectively. The study described in Example 1 aimed to develop a high redundancy non-obstructive assist device to provide mechanical circulatory support to the venous system in a failing Fontan circulation. The pump itself is intended to replace the interposition graft used for Fontans, which in case of pump failure reverts to an unassisted Fontan.

Methods: Solid and cored axial flow impellers (cored impellers having an axially extending void), sized to match the diameter of the venous flow path, supported on bearings and driven through a magnetic coupling by an external motor were used to optimize the impeller design. Impeller designs were further refined using Computational Fluid Dynamics (CFD) studies. Improved performance and low blood shear stresses were demonstrated by the CFD studies. A demonstrator pump prototype was built and used to test hydraulic performance and static pressure drop.

Figure 18A:
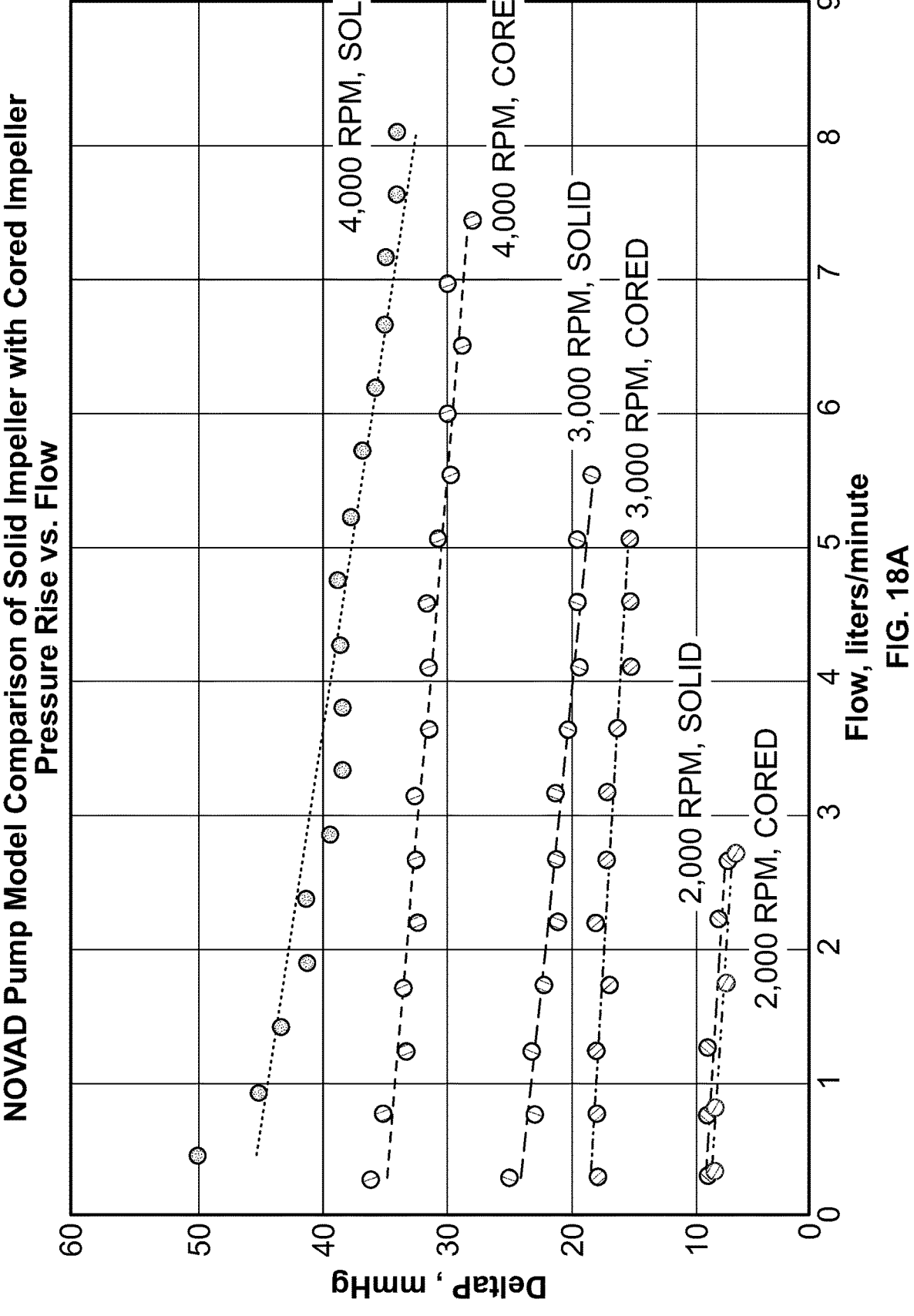
FIG. 18A is a graph comparing pressure rise across the pump (AP in mmHg) vs. flow (liters/min, LPM) at various pump speeds (rotations per min/RPM) for pumps with solid and cored impeller designs.
Figure 18B:
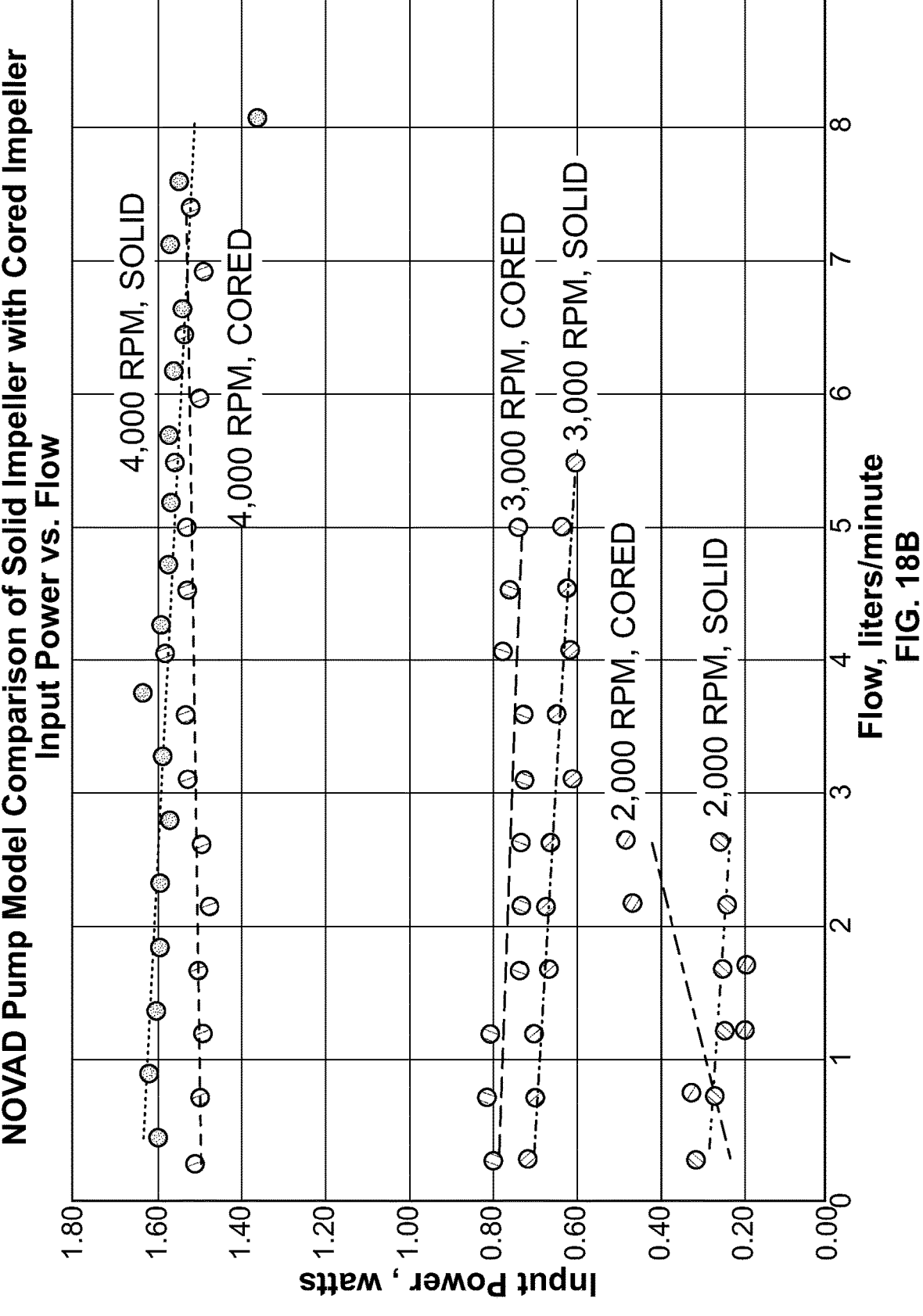
FIG. 18B is a graph comparing input power (Watts) vs. flow (LPM) at various pump speeds for pumps with solid and cored impeller designs.
Figure 18C:
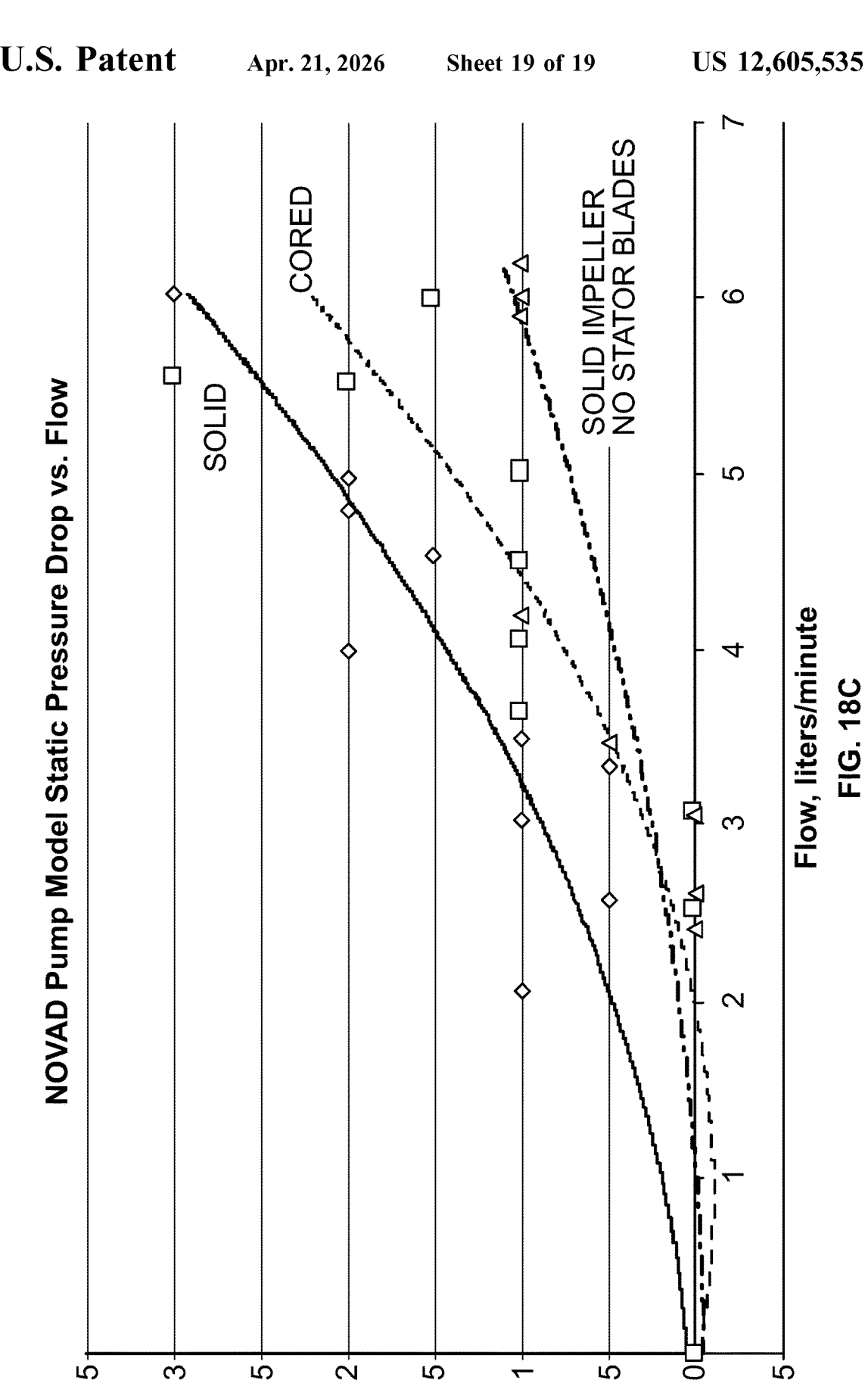
FIG. 18C is a graph comparing static pressure drop vs. flow for pumps with solid and cored impeller designs

Results: Desirable performance criteria were set as: hydraulic performance (flow≥3 L/min with pressure≥15 mmHg), static pressure drop (≤3 mmHg for flow up to 3 L/min), hemolysis no greater than other pediatric continuous flow devices, and long-term durability (wear and tear after 3 months of use). CFD studies were used to design impellers to satisfy the first two feasibility criteria. An impeller test fixture was used evaluate rapid-prototype impellers to support and validate the CFD studies and to allow detailed design analysis and sizing of the other demonstrator design elements. The demonstrator pump met hydraulic performance and static pressure drop criteria power, pressure and flow characteristics similar to pediatric continuous flow devices (FIG. 18A-C). Lower but still fully acceptable hydraulic performance with lower static pressure drops (<1 mmHg at 4L passive flow) were obtained with a cored compared to solid impeller design (FIG. 18F). A titanium prototype has now been built and duplicates the hydraulic performance while improving on the static pressure drop. Hemocompatibility and durability testing is to be performed.

Conclusions: A high redundancy venous assist device meets threshold criteria needed for mechanical support of Fontan circulation. The device when substituted for a Fontan conduit would act as a propulsive conduit, and a passive conduit when not in use. A similar device in the SVC or by itself in a reconfigured Fontan with a single pulmonary artery inflow would allow assistance of the entire venous circuit. This novel design needs further evaluation with a clinical prototype in in-vivo studies.

While the invention has been described with reference to particular embodiments and implementations, it will understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Therefore, it is intended that the invention not be limited to the particular implementations disclosed herein, but that the invention will include all implementations falling within the scope of the appended claims.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various implementations with various modifications as are suited to the particular use contemplated.

REFERENCES

1. STS Executive Summaries/Fall 2015 Harvest-Children [http://www.sts.org/sts-national-database/database-managers/executive-summaries]
2. Sinha P, Zurakowski D, He D, Yerebakan C, Freedenberg V, Moak J P, Jonas R A: Intra/extracardiac fenestrated modification leads to lower incidence of arrhythmias after the Fontan operation. *The Journal of thoracic and cardiovascular surgery* 2013, 145(3):678-682.
3. Anderson P A W, Sleeper L A, Mahony L, Colan S D, Atz A M, Breitbart R E, Gersony W M, Gallagher D, Geva T, Margossian R et al: Contemporary Outcomes After the Fontan Procedure A Pediatric Heart Network Multicenter Study. *Journal of the American College of Cardiology* 2008, 52(2):85-98.

4. Diller G-P, Giardini A, Dimopoulos K, Gargiulo G, Miller J, Derrick G, Giannakoulas G, Khambadkone S, Lammers A E, Picchio F M et al: Predictors of morbidity and mortality in contemporary Fontan patients: results from a multicenter study including cardiopulmonary exercise testing in 321 patients. *European Heart Journal* 2010, 31(24):3073-3083.

5. Khairy P, Fernandes S M, Mayer J E, Jr., Triedman J K, Walsh E P, Lock J E, Landzberg M J: Long-term survival, modes of death, and predictors of mortality in patients with Fontan surgery. *Circulation* 2008, 117(1):85-92.

6. Paridon S M, Mitchell P D, Colan S D, Williams R V, Blaufox A, Li J S, Margossian R, Mital S, Russell J, Rhodes J: A Cross-Sectional Study of Exercise Performance During the First 2 Decades of Life After the Fontan Operation. *Journal of the American College of Cardiology* 2008, 52(2):99-107.

7. Stephenson E A, Lu M, Berul C I, Etheridge S P, Idriss S F, Margossian R, Reed J H, Prakash A, Sleeper L A, Vetter V L et al: Arrhythmias in a contemporary fontan cohort: prevalence and clinical associations in a multicenter cross-sectional study. *Journal of the American College of Cardiology* 2010, 56(11):890-896.

8. d'Udekem Y, Iyengar A J, Cochrane A D, Grigg L E, Ramsay J M, Wheaton G R, Penny D J, Brizard C P: The Fontan Procedure: Contemporary Techniques Have Improved Long-Term Outcomes. *Circulation* 2007, 116 (11 suppl):I-157-I-164.

9. Rose E A, Gelijns A C, Moskowitz A J, Heitjan D F, Stevenson L W, Dembitsky W, Long J W, Ascheim D D, Tierney A R, Levitan R G et al: Long-Term Use of a Left Ventricular Assist Device for End-Stage Heart Failure. *New England Journal of Medicine* 2001, 345(20):1435-1443.

10. Slaughter M S, Rogers J G, Milano C A, Russell S D, Conte J V, Feldman D, Sun B, Tatooles A J, Delgado R M, Long J W et al: Advanced Heart Failure Treated with Continuous-Flow Left Ventricular Assist Device. *New England Journal of Medicine* 2009, 361(23):2241-2251.

11. Kirklin J K, Naftel D C, Pagani F D, Kormos R L, Stevenson L, Miller M, Young J B: Long-term mechanical circulatory support (destination therapy): on track to compete with heart transplantation?*The Journal of thoracic and cardiovascular surgery* 2012, 144(3):584-603; discussion 597-588.

12. Park S J, Milano C A, Tatooles A J, Rogers J G, Adamson R M, Steidley D E, Ewald G A, Sundareswaran K S, Farrar D J, Slaughter M S et al: Outcomes in Advanced Heart Failure Patients With Left Ventricular Assist Devices for Destination Therapy/Clinical Perspective. *Circulation: Heart Failure* 2012, 5(2):241-248.

13. Rodefeld M D, Coats B, Fisher T, Giridharan G A, Chen J, Brown J W, Frankel S H: Cavopulmonary assist for the univentricular Fontan circulation: von Karman viscous impeller pump. The Journal of thoracic and cardiovascular surgery 2010, 140(3):529-536.

14. Sinha P, Deutsch N, Ratnayaka K, Lederman R, He D, Nuszkowski M, Montague E, Mikesell G, Ishibashi N, Zurakowski D, Jonas R. Effect of mechanical assistance of the systemic ventricle in single ventricle circulation with cavopulmonary connection. The Journal of thoracic and cardiovascular surgery. 2014; 147:1271-1275

15. McCrindle B W, Manlhiot C, Cochrane A, et al. Factors associated with thrombotic complications after the Fontan procedure: a secondary analysis of a multicenter, randomized trial of primary thromboprophylaxis for 2 years after the Fontan procedure. Journal of the American College of Cardiology 2013 Jan. 22; 61(3):346-53.

16. Giridharan G A, Koenig S C, Kennington J, Sobieski M A, Chen J, Frankel S H, Rodefeld M D. Performance evaluation of a pediatric viscous impeller pump for Fontan cavopulmonary assist. J Thorac Cardiovasc Surg. 2013 January; 145(1):249-57. 22421403

17. Giridharan G A, Ising M, Sobieski M A, Koenig S C, Chen J, Frankel S, Rodefeld M D. Cavopulmonary assist for the failing Fontan circulation: impact of ventricular function on mechanical support strategy. ASAIO J. 2014 November-December; 60(6):707-15.

18. Rodefeld M D, Boyd J H, Myers C D, LaLone B J, Bezruczko A J, Potter A W, Brown J W. Cavopulmonary assist: circulatory support for the univentricular Fontan circulation. Ann Thorac Surg. 2003 December; 76(6): 1911-6; discussion 1916

19. Chopski S G, Fox C S, McKenna K L, Riddle M L, Kafagy D H, Stevens R M, Throckmorton A L. Physics-driven impeller designs for a novel intravascular blood pump for patients with congenital heart disease. Med Eng Phys. 2016 July; 38(7):622-32.

20. Kafagy D H, Dwyer T W, McKenna K L, Mulles J P, Chopski S G, Moskowitz W B, Throckmorton A L. Design of axial blood pumps for patients with dysfunctional fontan physiology: computational studies and performance testing. Artif Organs. 2015 January; 39(1):34-42.

21. Chopski S G, Rangus O M, Moskowitz W B, Throckmorton A L. Experimental measurements of energy augmentation for mechanical circulatory assistance in a patient-specific Fontan model. Artif Organs. 2014 September; 38(9):791-9.

22. Lacour-Gayet F G, Lanning C J, Stoica S, Wang R, Rech B A, Goldberg S, Shandas R. An artificial right ventricle for failing fontan: in vitro and computational study. Ann Thorac Surg. 2009 July; 88(1):170-6.

What is claimed is:

1. A circulation assist device comprising;

an inlet, an outlet, a central longitudinal axis extending between the inlet and the outlet, and a central lumen extending between the inlet and the outlet along the central longitudinal axis, a stator having at least one stator coil, a rotor positioned radially inward of the stator, the rotor having at least one rotor magnet, a stationary impeller housing positioned radially inward of the rotor, and an impeller positioned radially inward of the impeller housing, the impeller driven by rotation of the rotor, the impeller comprising at least one impeller blade and at least partially defining a lumen of the circulation assist device, wherein the impeller is configured to minimize a forward static pressure drop between the inlet and the outlet of the circulation assist device when the impeller is stationary, such the forward static pressure drop approximates the pressure drop between the inferior vena cava and central pulmonary artery of the unassisted Fontan circulation, wherein activation of the at least one stator coil causes rotation of the rotor relative to the stator, thereby driving rotation of the impeller, and wherein the impeller and the rotor rotate with respect to the stationary impeller housing and the stator.

2. The circulation assist device of claim 1, wherein the impeller is positioned radially inward from the rotor, and the impeller further comprises a radially external side and a radially internal side, a portion of the radially internal side being radially spaced from a central longitudinal axis and at least partially defining the central lumen.

3. The circulation assist device of claim 1, wherein the forward static pressure drop is no greater than 5 mmHg for flows up to 3 L/min when the impeller is stationary.

4. The circulation assist device of claim 1, wherein the circulation assist device is configured to give a forward pressure rise of greater than 10 mmHg when the impeller is rotating.

5. The circulation assist device of claim 1, wherein the rotor comprises a drive magnet and the at least one impeller blade comprises a driven magnet radially offset from the drive magnet that magnetically couples to the drive magnet such that rotation of the rotor synchronizes with rotation of the impeller.

6. The circulation assist device of claim 5, wherein the magnetic coupling between the drive and driven magnets offsets a hydraulic thrust on the impeller.

7. The circulation assist device of claim 5, wherein the impeller housing further comprises a sealing wall positioned between the rotor and the impeller, the sealing wall configured to isolate blood traveling through the central lumen from the rotor and the stator.

8. The circulation assist device of claim 1, wherein a leading edge of the impeller blade has a varying attack angle relative to the central longitudinal axis, such that the blade velocity at any radius approximates the laminar velocity of entering blood at that radius.

9. The circulation assist device of claim 8, further comprising an attack angle formed between an upstream surface of the impeller blade and the central longitudinal axis, wherein the attack angle varies radially.

10. The circulation assist device of claim 8, wherein a helix angle of the impeller blade varies longitudinally.

11. The circulation assist device of claim 8, wherein a thickness of the impeller blade is greater at a radially external side than a radially internal side.

12. The circulation assist device of claim 1, wherein the impeller is supported radially by a hydrodynamic bearing.

13. The circulation assist device of claim 1, wherein the impeller comprises an axle coupled to the at least one impeller blade, wherein a length of the axle is shorter than a length of the impeller.

14. The circulation assist device of claim 13, wherein the axle is a first axle, and the impeller further comprises a second axle longitudinally spaced from the first axle.

15. The circulation assist device of claim 14, wherein the impeller blade is coupled to the first axle, bridges an axially extending void between the first and second axle, and couples to the second axle.

16. The circulation assist device of claim 13, wherein the axle is configured to provide an axial thrust stop in cooperation with a stationary stop on the impeller housing.

17. The circulation assist device of claim 13, wherein the circulation assist device further comprises an axle support that stabilizes the impeller axle along the central longitudinal axis.

18. The circulation assist device of claim 1, wherein the impeller housing comprises at least one stationary guide vane positioned at the inlet or the outlet.

19. The circulation assist device of claim 1, wherein the components of the rotor and the impeller are integrated into a single component.

\* \* \* \* \*